United States Patent
Fosmer et al.

(10) Patent No.: US 10,731,184 B2
(45) Date of Patent: Aug. 4, 2020

(54) GENETICALLY MODIFIED YEASTS AND FERMENTATION PROCESSES USING GENETICALLY MODIFIED YEASTS

(71) Applicant: CARGILL, INCOPORATED, Wayzata, MN (US)

(72) Inventors: Arlene M. Fosmer, Eden Prairie, MN (US); Peter Alan Jauert, Minneapolis, MN (US); Gregory M. Poynter, St. Paul, MN (US); Brian J. Rush, Minneapolis, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 15/778,873

(22) PCT Filed: Nov. 22, 2016

(86) PCT No.: PCT/US2016/063401
§ 371 (c)(1),
(2) Date: May 24, 2018

(87) PCT Pub. No.: WO2017/091610
PCT Pub. Date: Jun. 1, 2017

(65) Prior Publication Data
US 2018/0346939 A1     Dec. 6, 2018

Related U.S. Application Data

(60) Provisional application No. 62/259,531, filed on Nov. 24, 2015.

(51) Int. Cl.
| | |
|---|---|
| *C12P 7/14* | (2006.01) |
| *C12P 7/06* | (2006.01) |
| *C12N 15/81* | (2006.01) |
| *C12P 7/56* | (2006.01) |

(52) U.S. Cl.
CPC .............. *C12P 7/14* (2013.01); *C12N 15/815* (2013.01); *C12P 7/06* (2013.01); *C12P 7/56* (2013.01); *C12Y 302/01026* (2013.01); *C12Y 503/01005* (2013.01); *Y02E 50/17* (2013.01)

(58) Field of Classification Search
CPC .............. C12P 7/14; C12P 7/56; C12N 15/815
See application file for complete search history.

(56) References Cited

U.S. PATENT DOCUMENTS

| | | |
|---|---|---|
| 5,876,988 A | 3/1999 | Selten et al. |
| 8,097,448 B2 | 1/2012 | Suominen et al. |
| 2007/0031950 A1 | 2/2007 | Winkler |
| 2012/0171719 A1 | 7/2012 | Hong et al. |
| 2012/0214214 A1* | 8/2012 | Hara ................... C12N 9/0006 435/139 |
| 2014/0038253 A1 | 2/2014 | Jessen et al. |
| 2014/0256048 A1 | 9/2014 | Chen et al. |

FOREIGN PATENT DOCUMENTS

| | | |
|---|---|---|
| WO | 9914335 A1 | 3/1999 |
| WO | 0071738 A1 | 11/2000 |
| WO | 0242471 A2 | 5/2002 |
| WO | 2004099381 A2 | 11/2004 |
| WO | WO2007032792 * | 3/2007 |
| WO | 2010074577 A1 | 7/2010 |
| WO | 2012087964 A1 | 6/2012 |
| WO | 2014018757 A1 | 1/2014 |
| WO | 2017091610 A1 | 6/2017 |
| WO | 2017091614 A1 | 6/2017 |

OTHER PUBLICATIONS

Siso et al. 1996; Respirofermentative metabolism in Kluyveromyces lactis: Ethanol production and the Crabtree effect. Enzyme nd Microbiology Technology. 18: 585-591.*
Radecka et al. Jun. 30, 2015; Looking beyond *Saccharomyces*: the potential of non-conventional yeast species for desirable traits in bioethanol fermentation. FEMS Yeast Research. 15: 1-13.*
UCDavis, Viticulture & enology. Issatchenkia orientialis. 2018. On the web at: wineserver.ucdavis.edu/industry-info/enology/wine-microbiology/yeast-mold/issatchenkia-orientalis.*
Sreekrishna et al. 1987. Invertase gene (SUC2) of *Saccharomyces cerevisiae* as a dominant markder for the transformation of Pichia pastoris. Gene 59(1): 115-125, Abstract Only.*
Feng , et al., "The Relationship between Fermentation Activity of *Saccharomyces cerevisiae* in High-sugar Dough and Sucrase Activity", Modern Food Science and Technology, vol. 30, No. 5, 2014, 131-135.
Förster, André , et al., "Citric acid production from sucrose using a recombinant strain of the yeast *Yarrowia lipolytica*", Applied Microbiology and Biotechnology, Springer, Berlin, DE—ISSN 1432-0614 vol. 75, Issue 6. XP019513772, Apr. 20, 2007, 1409-1417.
Georis , et al., "Glucose repression of the Kluyveromyces lactis invertase gene K/INVi does not require Migip", Molecular and General Genetics, vol. 261, No. 4-5. XP008183240, Jun. 1999, 862-870.
H P Hsieh , "An autoseiection system in recombinant Kluyveromyces lactis enhances cloned gene stability and provides freedom in medium selection", XP055304987, Retrieved from the Internet: URL:http://rd.springer.com/content.pdf/10, Jan. 1, 1998, 147-152.
Jessica CM Gallardo , et al., "Enrichment of a continuous culture of *Saccharomyces cerevisiae* with the yeast *Issatchenkia orientalis* in the production of ethanol at increasing temperatures", Journal of Industrial Microbiology & Biotechnology : Official Journal of the Society for Industrial Microbiology. Springer, Berlin, DE, vol. 38, No. 3, XP019883458, Aug. 10, 2010, 405-414.

(Continued)

*Primary Examiner* — Karen Cochrane Carlson

(57) ABSTRACT

The present invention relates to a genetically engineered yeast capable of manufacturing a fermentation product using sucrose as a fermentation substrate, and fermentation processes using such a yeast. The yeast has an exogenous invertase gene and has a deletion or disruption of the PDC activity gene. Accordingly, the yeast is useful for manufacturing fermentation products other than ethanol from fermentation substrates containing sucrose.

19 Claims, 3 Drawing Sheets
Specification includes a Sequence Listing.

(56) References Cited

OTHER PUBLICATIONS

Jessica CM Gallardo, et al., "Ethanol production from molasses in co-cultures of Issatchenkia orientalis and *Saccharomyces cerevisiae* at 42° C.", XP055344048 Retrieved from the Internet: URL:http://conferencing.uwex.edu/conferences/icy2012/documents/ArealPosters.pdf, Aug. 26, 2012, 62.

Lazar, Zbigniew, et al., "Optimized invertase expression and secretion cassette for improving Yarrowia lipolytica growth on sucrose for industrial applications", J Ind Microbioi Biotechnol. 2013; 40(11) Published online: doi: 10.1007/s10295-013-1323-1, Sep. 6, 2013, 1273-1283.

Leonardo De Figueiredo Vilela, et al., "Functional expression of Burkholderia cenocepacia xylose isomerase in yeast increases ethanol production from a glucose-xylose blend", Bioresource Technology vol. 128, XP055278232, Oct. 16, 2012, 792-796.

Rajoka, et al., "Kinetics and thermodynamics of ethanol production by a thermotolerant mutant of *Saccharomyces cerevisiae* in a microprocessor-controlled bioreactor", Letters in Applied Microbiology vol. 40, No. 5. XP055344147, May 1, 2005, 316-321.

Bernhard, Susan L., et al., "Cysteine Analogs of Recombinant Barley Ribsosome Inactivating Protein Form Antibody Conjugates with Enhanced Stability and Potency in Vitro", Bioconjugate Chem. 1994, 5, 126-132.

Brat, Dawid, et al., "Functional Expression of a Bacterial Xylose Isomerase in Saccharomyces cerevisiae", Applied and Environmental Microbiology, Apr. 2009, p. 2304-2311.

De Deken, R. H., "The Crabtree Effect: A Regulatory System in Yeast", J. gen. Microbiol, (1966), 44, 149-156.

Gietz, Daniel, et al., "Improved method for high efficiency transformation of intact yeast cells", Nucleic Acids Research, vol. 20, No. 6, 1425.

Han, Byeong-Gu, et al., "Crystal structure of a class 2 D-xylose isomerase from the human intestinal tract microbe Bacteroides thetaiotaomicron", Biodesign, vol. 3, No. 1, pp. 41-47, 2015.

Ito, Wataru, et al., "A general method for introducing a series of mutations into cloned DNA using the polymerase chain reaction", Gene, 102 (1991) 67-70.

Kurtzman, Cletus P., et al., "Identification and phylogeny of ascomycetous yeasts from analysis of nuclear large subunit (26S) ribosomal DNA partial sequences", Antonie van Leeuwenhoek, vol. 73, 1998, 331-371.

Kurtzman, Cletus P., et al., "The Yeasts, A Taxonomic Study", Fourth Edition, Section 35, Issatchenkia Kudryavtsev, 1998, 222-223.

Kuyper, M, et al., "High-level functional expression of a fungal xylose isomerase: the key to efficient ethanolic fermentation of xylose by Saccharomyces cerevisiae?", FEMS Yeast Research, Wiley-Blackwell Publishing Ltd, GB, NL, Vol. 4 No. 1, XP002312913, Oct. 1, 2003, 69-78.

Lee, Sun-Mi, et al., "Directed Evolution of Xylose Isomerase for Improved Xylose Catabolism and Fermentation in the Yeast Saccharomyces cerevisiae", AEM, vol. 78, No. 16, pp. 5708-5716, Aug. -2012.

Lee, Sun-Mi, et al., "Systematic and evolutionary engineering of a xylose isomerase-based pathway in Saccharomyces cerevisiae for efficient conversion yields", Biotechnology for Biofuels 2014, 7:122.

Nielsen, Jens, et al., "Bioreaction Engineering Principles", Second Edition, Kluwer Academic/Plenum Publishers, equation 1, 2003, 449.

Silveira, M.C.F., et al "Assay for in Vivo Yeast Invertase Activity Using NaF", Analytical Biochemistry 238, 26-28 (1996).

Terpe, K., Overview of tag protein fusions: from molecular and biochemical fundamentals to commercial systems. Appl Microbiol Biotechnol 60, 523-533 (2003). https://doi.org/10.1007/s00253-002-1158-6.

Vallette, Francois, et al., "Construction of mutant and chimeric genes using the polymerase chain reaction"; Nucleic Acids Research, vol. 17, Issue 2. Jan. 25, 1989, pp. 723-733, https://doi.org/10.1093/nar/17.2.723.

Vangrysperre, W., et al., "Single active-site histidine in D-xylose isomerase from Streptomyces violaceoruber", Biochem, J. 263. 1989, 195-199.

Verduyn, Cornelis, et al., "Effect of Benzoic Acid on Metabolic Fluxes in Yeasts: A Continuous-Culture Study on the Regulation of Respiration and Alcoholic Fermentation", Yeast, vol. 8, 1992, 501-517.

Higuchi, R., "PCR Protocols: A Guide to Methods and Applications", A.I Michael, D.H. Gelfand, D.J. Sninsky and T.J. White (eds.), Academic Press, pp. 177-183, 1990.

\* cited by examiner

GENETICALLY MODIFIED YEASTS AND FERMENTATION PROCESSES USING GENETICALLY MODIFIED YEASTS

CROSS-REFERENCE TO RELATED APPLICATIONS

This application is a national phase application of international application PCT/US2016/063401, filed Nov. 22, 2016, and entitled GENETICALLY MODIFIED YEASTS AND FERMENTATION PROCESS USING GENETICALLY MODIFIED YEASTS, which application claims benefit of U.S. Provisional Patent Application Ser. No. 62/259,531, filed Nov. 24, 2015, entitled GENETICALLY MODIFIED YEASTS AND FERMENTATION PROCESS USING GENETICALLY MODIFIED YEASTS, both of which applications are hereby incorporated by reference in its entirety.

SEQUENCE LISTING

The entire contents of the ASCII text file entitled "N00316_US_PCT[2]ST25.txt," created on May 24, 2018, and having a size of 82 kilobytes is hereby incorporated herein by reference in its entirety.

BACKGROUND OF THE INVENTION

Industrial yeast fermentation processes often use glucose-based substrates in regions of the world where such substrates are readily available. For example, glucose syrup made from corn starch is commonly used in fermentation processes in the United States. However, in some regions, sucrose substrates are more readily available and/or more economical for use in fermentation processes, or it is desirable to use such sucrose substrates as a supplement to glucose substrates.

SUMMARY OF THE INVENTION

Described herein are genetically engineered yeasts useful for manufacturing fermentation products and fermentation processes based on the use of such yeasts. In one aspect, the present invention relates to engineering yeasts to use sucrose as a fermentation substrate from host yeasts that are incapable of using sucrose or are inefficient at using sucrose as a fermentation substrate. Accordingly, the yeasts of the present invention have a functional invertase gene. In one aspect, the yeasts are engineered to include promoters that are associated with an optimized expression of invertase.

In one aspect, the genetically engineered yeast comprises a yeast capable of producing a fermentation product at a production rate of at least 1.0 grams/liter-hour (g L$^{-1}$ h$^{-1}$), wherein the genetically engineered yeast has a functional invertase gene and has a deletion or disruption of the pyruvate decarboxylase (PDC) gene. In some embodiments, the yeast is capable of producing a fermentation product at a fermentation production rate of at least 1.5 g L$^{-1}$ h$^{-1}$ or at least 2.0 g L$^{-1}$ h$^{-1}$. In some embodiments, the yeast is capable of producing a fermentation product at a pathway fermentation yield of at least 55 percent, at least 65 percent, at least 70 percent, or at least 75 percent. In some embodiments, the yeast is capable of producing a fermentation product at a final titer of at least 30 g/liter, at least 80 g/liter, or at least 100 g/liter. In some embodiments, the yeast has a ratio of invertase activity to glucose capacity of less than 95, less than 30, or less than 20. In some embodiments, the yeast has a ratio of invertase activity to glucose capacity of at least 0.95 or at least 10. In some embodiments, the yeast has a ratio of invertase activity to glucose capacity of at least 2.5, 3, or 5.

In another aspect, the genetically engineered yeast capable of manufacturing a fermentation product is a yeast of the *I. orientalis/P. fermentans* clade having a gene encoding a functional invertase. In one embodiment, such a yeast is PDC-negative. In one embodiment, the yeast is *I. orientalis*.

In some embodiments, the yeast is Crabtree-negative. In some embodiments, the functional invertase gene is selected from the group consisting of SEQ ID NO: 6; SEQ ID NO: 15; SEQ ID NO: 16; and SEQ ID NO: 17. In some embodiments, the yeast includes an exogenous or artificial promoter for the functional invertase gene. In some embodiments, the promoter is selected from the group consisting of Pyruvate decarboxylase, Glyceraldehyde-3-phosphate dehydrogenase, Translational elongation factor, Transaldolase, RPL16B, 3-phosphoglycerate kinase, and Enolase. In some embodiments, the yeast is capable of manufacturing any of the following fermentation products: lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, or acetic acid, or any derivatives thereof, any salts thereof, or any combinations thereof.

In one aspect, the process is a process for manufacturing a fermentation product comprising fermenting a substrate using any of the genetically engineered yeasts described herein. In one aspect, the process is a process for manufacturing a fermentation product comprising: fermenting a substrate using a yeast, wherein the substrate includes sucrose and the yeast includes an exogenous invertase gene.

In some embodiments, the process is microaerobic. In some embodiments, the volumetric oxygen uptake rate (OUR) is 0.5 to 40 mmol O$_2$/(L·h), 1 to 30 mmol O$_2$/(L·h), 3 to 20 mmol O$_2$/(L·h), or 5 to 16 mmol O$_2$/(L·h). In some embodiments, the specific OUR is 0.2 to 13 mmol O$_2$/(g cell dry weight·h), 0.3 to 10 mmol O$_2$/(g cell dry weight·h), 1 to 7 mmol O$_2$/(g cell dry weight·h), or 2 to 6 mmol O$_2$/(g cell dry weight·h).

In some embodiments, the fermentation cell concentration of the process is 1 to 10 g cell dry weight/L, 2 to 8 g cell dry weight/L, or 2.5 to 6 g cell dry weight/L. In some embodiments, the pitch density of the process is 0.05 to 5 g cell dry weight/L, 0.05 to 4 g cell dry weight/L, or 0.05 to 2 g cell dry weight/L. In some embodiments, the fermentation temperature is in the range of 25 to 45° C., in the range of 20 to 40° C., or in the range of 33 to 38° C. In some embodiments, the fermentation substrate of the process comprises sucrose, glucose, hydrozylates of starch, xylose, lignocellulosic hydrozylates, or any mixture or any combination thereof.

In some embodiments, the process has a ratio of invertase activity to glucose consumption rate of less than 95, of less than 30, or of less than 20. In some embodiments, the process has a ratio of invertase activity to glucose consumption rate of at least 0.95 or at least 10. In some embodiments, the fermentation yield of the process is at least 55 percent, at least 65 percent, at least 70 percent, or at least 75 percent. In some embodiments, the final titer is at least 30 g/liter, at least 80 g/liter, or at least 100 g/liter. In some embodiments, the fermentation product of the process is lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, or acetic acid, or any derivatives thereof, any salts thereof, or any combinations thereof.

In some embodiments, the invertase gene in the yeast is an integrated functional exogenous invertase gene. In some embodiments, the invertase activity of the yeast or the yeast in the process is at least 1, 2, 2.5, 3, 4, 5, 6, 7, 8, or 9 (g glucose released/(g CDW*h)). In some embodiments, the invertase activity of the yeast or the yeast in the process is less than 10, 15, 20, 30, 40, or 50 (g glucose released/(g CDW*h). In some embodiments, the invertase activity of the yeast or process is in the range of about 2.5-50, 5-30, or 5-20 (g glucose released/(g CDW*h)). In some embodiments, the ratio of invertase activity to glucose consumption rate (or glucose capacity) of the yeast or process is in the range of about 0.5 to 25 or 1 to 20.

It is also to be understood that the elements or aspects of any embodiment of the processes, methods, or compositions described above can be applied to any other embodiment, as would be understood by a person skilled in the art.

BRIEF DESCRIPTION OF THE DRAWINGS

The following detailed description of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
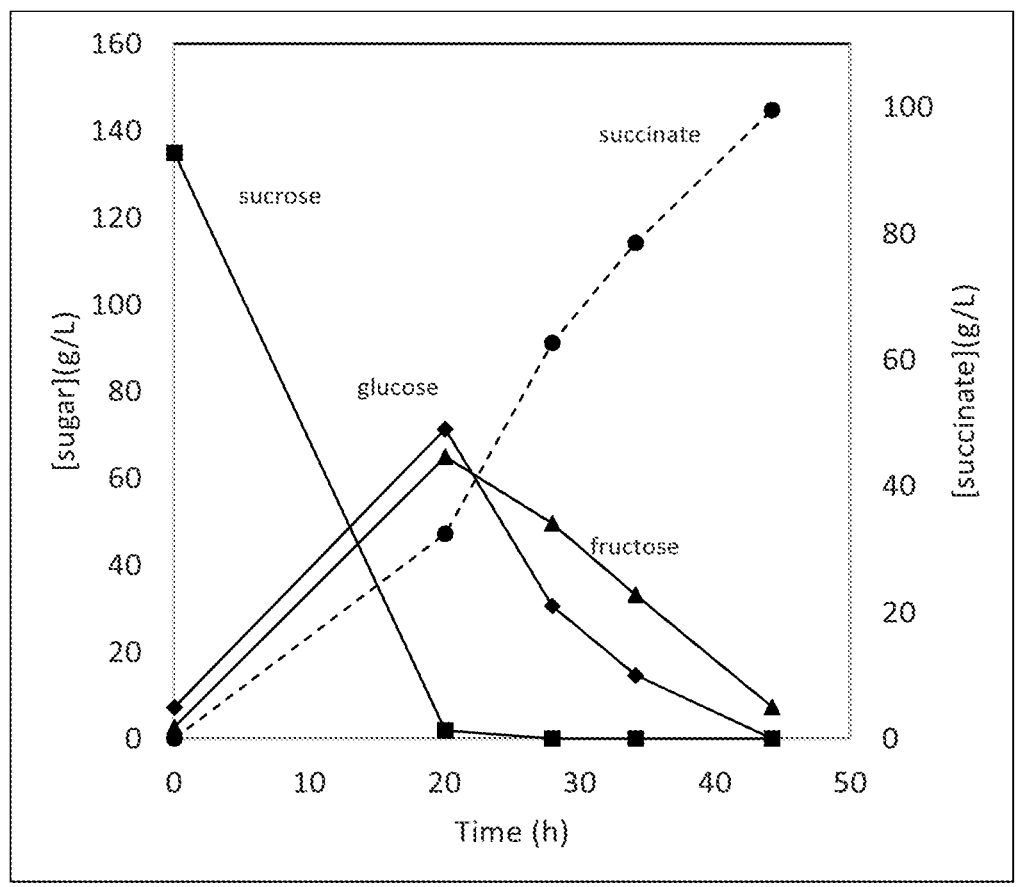
FIG. 1 is a graph showing sucrose (squares), glucose (diamonds), fructose (triangles), and succinate (circles) titers for an exemplary fermentation process using yeast strain 1-8.

It is to be understood that the figures and descriptions of the present invention provided herein have been simplified to illustrate elements that are relevant for a clear understanding of the present invention, while eliminating other elements found in the related field(s) of art. Those of ordinary skill in the art would recognize that other elements or steps may be desirable or required in implementing the present invention. However, because such elements or steps are well known in the art or do not facilitate a better understanding of the present invention, a discussion of such elements or steps is not provided herein.

Definitions

Unless defined otherwise, all technical and scientific terms used herein have the same meaning as commonly understood by one skilled in the art to which this invention belongs. As used herein, each of the following terms has the meaning associated with it as defined in this section.

Fermentation Process Definitions

As used herein, "inoculation" is defined as the point in time wherein a microorganism capable of producing a fermentation product is introduced into a fermentation medium. This is a term that is well known to those skilled in the art.

As used herein, "end of fermentation" is defined as the point in time where a fermentation process meets a predetermined criteria. The predetermined criteria can include any of the following: a predetermined time interval, exhaustion of the desired fraction of carbon source supplied, cessation of carbon source consumption, or cessation of fermentation product formation. In one embodiment, "end of fermentation" is defined as the point in time where harvesting of the bioproduct is started. As would be understood by a person skilled in the art, "end of fermentation" can refer to a point in time that is different depending on the scale and purpose of the fermentation process. For a large-scale production fermentation process, the "end of fermentation" is preferably the point at which harvesting of the bioproduct is started, i.e., after product formation has effectively stopped.

As used herein, "cell dry weight" refers to the concentration of dry cell mass present in a fermentation medium at the time of measurement, as measured in a fermentation sample. Cell dry weight is commonly expressed in units of grams/liter (g/L).

As used herein, "cell dry weight at inoculation" refers to the concentration of dry cell mass present in a fermentation medium immediately following inoculation, as measured in a fermentation sample. For fed-batch fermentations, the initial cell dry weight is calculated based on the final volume of fermentation medium. Measurement of dry cell weight is a method known to those skilled in the art. Cell dry weight at inoculation is commonly expressed in units of g/L.

As used herein, "cell dry weight at end of fermentation" refers to the concentration of dry cell mass present in a fermentation medium at the end of fermentation, as measured in a fermentation sample. Cell dry weight at end of fermentation is commonly expressed in units of g/L.

As used herein, "final titer" refers to the concentration of a substance in the fermentation broth at the end of fermentation. The final titer is commonly expressed in units of g/L.

As used herein, "initial titer" refers to the concentration of a substance present at inoculation. The initial titer is commonly expressed in units of g/L.

As used herein, "batch time" refers to the amount of time that has elapsed between the inoculation and the end of fermentation. The batch time is commonly expressed in units of hours (h).

As used herein, "sugar consumption rate" for a batch process refers to the difference between the initial titer of a sugar present in the fermentation broth and the final titer of the same sugar (initial titer minus final titer) divided by the batch time. The sugar consumption rate is commonly expressed in units of grams per liter-hour (g $L^{-1}$ $h^{-1}$, which can also be abbreviated as (g/(L*h))). When applied to a continuous or semi-continuous process, the "sugar consumption rate" is determined using methods known in the art.

As used herein, the "specific sugar consumption rate" for a batch process refers to the sugar consumption rate divided by the cell dry weight at the end of fermentation. The specific sugar consumption rate is commonly expressed in units of (g sugar) (g cells)$^{-1}$ $h^{-1}$. When applied to a continuous or semi-continuous process, the "specific sugar consumption rate" is determined using methods known in the art.

The sugar consumption rate and specific sugar consumption rate may be applied to specific sugars such as, for instance, glucose or sucrose. In these cases, one may refer to a glucose consumption rate, specific glucose consumption rate, sucrose consumption rate, or specific sucrose consumption rate.

As used herein, "fermentation production rate" for a batch process refers to the final titer minus initial titer of fermentation product (final titer minus initial titer) divided by the batch time. The production rate is commonly expressed in units of grams per liter-hour (g $L^{-1}$ $h^{-1}$). When applied to a continuous or semi-continuous process, the "fermentation production rate" is determined using methods known in the art.

As used herein, the "specific production rate" refers to the fermentation production rate divided by the cell dry weight at the end of fermentation. The specific production rate is commonly expressed in units of (g product) (g cells)$^{-1}$ $h^{-1}$. When applied to a continuous or semi-continuous process, the "specific production rate" is determined using methods known in the art.

As used herein, "product yield" of a fermentation product refers to a ratio of two quantities: a) mass of product (e.g., succinate) produced in the course of the fermentation (numerator) b) the mass of carbon source added to the fermentation (denominator). The product yield as a percentage is commonly expressed in units of gram per gram (g/g) times 100. Particular note should be taken that product yield is calculated as a ratio of masses. The mass of fermentation product produced should account for the mass of fermentation product present in the fermentation medium at the end of the batch, as well as the mass of any fermentation product harvested during the course of the batch, less the mass of fermentation product present at the start of batch, and further less the mass of any fermentation product added during the course of the batch. The mass of carbon source added to the batch should include the mass of all carbon source(s) present in the fermenter at the start of the batch in addition to the mass of any carbon source(s) added during the course of the batch.

As used herein, "oxygen uptake rate" ("OUR") refers to the volumetric rate at which oxygen is consumed during a fermentation. Inlet and outlet oxygen concentrations can be measured with exhaust gas analysis, for instance by mass spectrometers. OUR can be calculated by one of ordinary skill in the relevant arts using the Direct Method described in Bioreaction Engineering Principles 2nd Edition, 2003, Kluwer Academic/Plenum Publishers, p. 449, equation 1. It is commonly measured in units of (mmol $O_2$) $L^{-1}$ $h^{-1}$.

As used herein, "specific oxygen uptake rate" refers to the specific rate at which oxygen is consumed during a fermentation. It is calculated as the ratio of the OUR to the measured cell dry weight. It is commonly measured in units of mmol $O_2$ (g cell dry weight)$^{-1}$ $h^{-1}$.

As used herein, the term "microaerobic" refers to fermentation aeration conditions that are intermediate between fully aerobic and anaerobic conditions. Under microaerobic conditions, oxygen is supplied to the fermentation. Further, the oxygen is supplied at a rate such that the dissolved oxygen concentration is predominantly maintained below 5% of the saturation concentration of oxygen in the fermentation medium under air at atmospheric pressure. Under microaerobic conditions, the oxygen uptake rate is typically between 0.1 (mmol $O_2$) $L^{-1}$ $h^{-1}$ and 40 (mmol $O_2$) $L^{-1}$ $h^{-1}$ Yeast Characteristics Definitions As used herein, the term "Crabtree-negative" refers to a yeast cell having a Crabtree-negative phenotype, i.e., any yeast cell that does not exhibit the Crabtree effect. In one embodiment, the host cell of the present invention is a Crabtree-negative yeast. The Crabtree effect concerns the inhibition of synthesis of respiratory enzymes. The Crabtree effect is defined as the occurrence of fermentative metabolism under aerobic conditions as a result of the inhibition of oxygen consumption by a microorganism when cultured at high specific growth rates (long-term effect) or in the presence of high concentrations of glucose (short-term effect). Organisms with the Crabtree negative phenotype do not exhibit this effect, and are thus able to consume oxygen even in the presence of high concentrations of glucose or at high growth rates. Whether an organism is Crabtree positive or Crabtree negative can be determined by comparing the ratio of fermented glucose to respired glucose during cultivation under aerobic conditions, with a ratio of greater than 1 indicative of a Crabtree positive organism (e.g., see De Deken, R. H. (1965) J. gen. Microbiol., 44:149-156).

As used herein, "sugar capacity" refers to the rate at which a yeast consumes a sugar as measured according to the method titled "strain capacity evaluation" as described below. The sugar capacity refers to the difference between the initial titer of a sugar present in the fermentation broth and the titer of the same sugar at the end of the evaluation (initial titer minus end titer) divided by the batch time, further divided by the cell dry weight at the end of the evaluation. The sugar capacity is commonly expressed in units of (g sugar) (g cells)$^{-1}$ $h^{-1}$. This assay can be used to measure the sugar capacity for a number of sugars such as glucose or sucrose, resulting in, for example, a measurement of "glucose capacity" or "sucrose capacity."

$$\text{sugar capacity} = \frac{[\text{sugar}]_{initial} - [\text{sugar}]_{end\ of\ evaluation}}{(\text{batch time}) \times (\text{cell dry weight at end of evaluation})}$$

For example, in an evaluation that lasts 45 hours, with 140.0 g/L glucose present at inoculation, 1.0 g/L glucose present at the end of the evaluation, and 6.0 g/L cell dry weight of yeast present at the end of fermentation, the calculated glucose capacity is 0.51 g glucose $g^{-1}$ cells $h^{-1}$.

As used herein, "product capacity" refers to the rate at which a yeast produces a fermentation product as measured according the method titled "strain capacity evaluation" as described below. The product capacity refers to the difference between the initial titer of a product present in the fermentation broth and the titer of the same product at the end of the evaluation (initial titer minus end titer) divided by the batch time, further divided by the cell dry weight at the end of the evaluation. The product capacity is commonly expressed in units of (g product) (g cells)$^{-1}$ $h^{-1}$. This assay can be used to measure the product capacity for a number of products such as lactate or succinate, resulting in a measurement of, for example, "lactate capacity" or "succinate capacity."

$$\text{product capacity} = \frac{[\text{product}]_{end\ of\ evaluation} - [\text{product}]_{initial}}{(\text{batch time}) \times (\text{cell dry weight at end of evaluation})}$$

For example, in an evaluation that lasts 45 hours, with 0.0 g/L succinate present at inoculation, 100.0 g/L succinate present at the end of the evaluation, and 6.0 g/L cell dry weight of yeast present at the end of fermentation, the calculated succinate capacity is 0.37 g glucose $g^{-1}$ cells $h^{-1}$.

As used herein, "ratio of invertase activity to glucose capacity" refers to the ratio of invertase activity of a yeast strain, as measured according to the "invertase activity evaluation" method described below, to the observed glucose capacity of the same strain, as measured according to the "strain capacity evaluation" method described below.

The units of this parameter are (g glucose released from sucrose hydrolysis/(g cell dry weight*hour))/(g glucose consumed/(g cell dry weight*hour)).

In certain embodiments, the genetically modified yeast cells provided herein further comprise a deletion or disruption of one or more native genes. As used herein, the phrase "deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. The phrase "deletion or disruption" with regard to a metabolic pathway means that the pathway is either inoperative or else exhibits activity that is reduced by at least 75%, at least 85%, or at least 95% relative to the native pathway. In certain embodiments, deletion or disruption of a native metabolic pathway is accomplished by incorporating one or more genetic modifications that result in decreased expression of one or more native genes that reduce ethanol production.

In some embodiments, deletion or disruption of native genes can be accomplished by forced evolution, mutagenesis, or genetic engineering methods, followed by appropriate selection or screening to identify the desired mutants. In some embodiments, deletion or disruption of a native host cell gene can be coupled to the incorporation of one or more exogenous genes into the host cell, i.e., the exogenous genes can be incorporated using a gene expression integration construct that is also a deletion construct. In some embodiments, deletion or disruption can be accomplished using a deletion construct that does not contain an exogenous gene or by other methods known in the art.

In some embodiments, the modified yeast cells described herein have a deletion or disruption of one or more native genes encoding an enzyme involved in ethanol fermentation or consumption, including for example pyruvate decarboxylase (PDC, catalyzes the conversion of pyruvate to acetaldehyde and carbon dioxide). Such modifications decrease the ability of the yeast cell to produce ethanol, thereby maximizing fermentation product production. In some embodiments where the modified yeast cell is *I. orientalis*, the cells comprise a deletion or disruption of a PDC gene encoding the amino acid sequence of SEQ ID NO: 14 and/or a gene encoding an amino acid sequence with at least 50%, at least 60%, at least 70%, at least 80%, at least 85%, at least 90%, at least 95%, at least 97%, or at least 99% sequence identity to the amino acid sequence of SEQ ID NO: 14.

As used herein, the terms "PDC-negative" or "PDC-" refer to a yeast which has a deletion or disruption of the pyruvate decarboxylase (PDC) gene. As would be understood by a person skilled in the art, deletion or disruption of the PDC gene will eliminate or reduce expression of PDC enzyme, which is an enzyme necessary for the production of ethanol via fermentation. In one embodiment, the pyruvate decarboxylase activity of the yeast is less than 0.05 U/milligram of total protein when using the methods previously described by Michele M. Bianchi, Lorenza Tizzani, Monika Destruelle, Laura Frontal and Micheline Wesolows ki-Louvel, The 'petite-negative' yeast *Kluyveromyces lactis* has a single gene expressing pyruvate decarboxylase activity.

(1996) Molecular Microbiology, 19 (1): 27-36. Biomass used for the assay is grown in YP media with 2% glucose. The activity unit (U) is defined as the amount of activity required for the conversion of 1 micromole of substrate (in this example, NADH to NAD+) per minute.

The term "exogenous" as used herein with regard to genetic components means that the genetic component is present in a modified version of a microorganism, but is not present in the genome of a native form of the particular microorganism cell. In some embodiments, the exogenous genetic component can be a modified form of a component that was native to the cell, it can be derived from another organism, it can be a modified form of a component derived from another organism, or it can be a synthetically-derived component. For example, the *K. lactis* invertase gene is exogenous when introduced into *I. orientalis*.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, -2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 7 should be considered to have specifically disclosed subranges such as from 1 to 3, from 1 to 4, from 1 to 6, from 2 to 5, from 3 to 5, etc., as well as individual numbers within that range, for example, 1, 2, 3, 3.6, 4, 5, 5.8, 6, 7, and any whole and partial increments in between. This applies regardless of the breadth of the range.

Description

Described herein are genetically modified yeast strains useful for manufacturing a fermentation product and fermentation processes using these yeasts. The yeast strains are modified to include a functional exogenous invertase gene.

Accordingly, in one embodiment, the present invention relates to a yeast strain useful for fermentation processes having sucrose as a substrate. The yeast strain is preferably PDC-negative, and therefore can be useful for manufacturing fermentation products other than ethanol, for example succinic acid. In one embodiment, the yeast is Crabtree negative.

As contemplated herein, sucrose-based fermentation processes would preferably use a yeast expressing the invertase enzyme. However, invertase expression is not native to many yeasts that are desirable for industrial fermentation processes. Feng et al., describe the relationship between the fermentation activity of *Saccharomyces cerevisiae* in high-sugar dough and sucrase activity (Modern Food Sci. and Tech., 2014, 30:131-135). However, *S. cerevisiae* is primarily used for the production of ethanol, i.e., it has pyruvate decarboxylase (PDC) activity, and it is less desirable for use in manufacturing many other types of industrial chemicals. As would be understood by a person of ordinary skill in the art, deletion or disruption of the PDC gene in *S. cerevisiae* is highly problematic. This deletion in *S. cerevisiae* results in the loss of the ability to grow on glucose, as well as causing an autotrophy for C2 compounds (Flikweert et al., Growth requirements of pyruvate-decarboxylase-negative *Saccharomyces cerevisiae*, FEMS Microbiol Lett 1999; 174 (1):73-9).

Genetically Engineered Yeast

The genetically modified yeast of the present invention is made by performing one or more genetic modifications to a host yeast cell. In some embodiments, the host yeast cell lacks a native invertase. In some embodiments, the host yeast cell does not include a nucleic acid encoding a polypeptide with a sequence that has greater than 70% identity with SEQ ID NO: 6, SEQ ID NO: 15, SEQ ID NO: 16, or SEQ ID NO: 17. In some embodiments, the host yeast cell cannot grow on sucrose as a sole carbon source. In some embodiments, the host yeast cell has a maximum specific growth rate on (YNB+20 g/L glucose) media that exceeds $0.15$ $h^{-1}$ and a maximum specific growth rate on (YNB+20 g/L sucrose) media that is less than $0.05$ $h^{-1}$. In some embodiments, the host yeast is a Crabtree-negative yeast.

In some embodiments, the genetically modified yeast cells described herein belong to the genus *Issatchenkia*, and in some such embodiments the yeast cells are *I. orientalis*. When first characterized, the species *I. orientalis* was assigned the name *Pichia kudriavzevii*. *I. orientalis* yeasts have also been described in the art as *C. krusei*. Numerous additional synonyms for the species *I. orientalis* have been described (see Kurtzman and Fell, The Yeasts, a Taxonomic Study, Section 35, *Issatchenkia Kudryavtsev*, pp. 222-223 (1998), which is hereby incorporated by reference).

The *I. orientalis/P. fermentans* clade is the most terminal clade that contains at least the species *I. orientalis*, *Pichia galeiformis*, *Pichia sp.* YB-4149 (NRRL designation), *Candida ethanolica*, *Pichia deserticola*, *P. membranifaciens*, and *P. fermentans*. Members of the *I. orientalis/P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," *Antonie van Leeuwenhoek* 73:331-371, 1998, which is hereby incorporated by reference (see especially p. 349). Analysis of the variable D1/D2 domain of the 26S ribosomal DNA from hundreds of ascomycetes has shown that the *I. orientalis/P. fermentans* clade contains very closely related species. Members of the *I. orientalis/P. fermentans* clade exhibit greater similarity in the variable D1/D2 domain of the 26S ribosomal DNA to other members of the clade than to yeast species outside of the clade. Therefore, other members of the *I. orientalis/P. fermentans* clade can be identified by comparison of the D1/D2 domains of their respective ribosomal DNA, and comparing to that of other members of the clade and closely related species outside of the clade, using Kurtzman and Robnett's methods.

As described herein, the present invention relates to genetically modified yeasts of the *I. orientalis/P. fermentans* clade, preferably *I. orientalis*. However, the present invention is not limited to using any specific yeast such as *I. orientalis*, and the host yeast cell can be any suitable yeast strain, as would be understood by a person skilled in the art. To genetically modify the yeast cell, a suitable locus is selected for gene integration. One of ordinary skill in the art would know how to select suitable loci in a yeast genome for gene integration. An example of a suitable locus for integration of exogenous genes in *I. orientalis* includes, but is not limited to, locus A, which is flanked by SEQ ID NO: 1 and SEQ ID NO: 2. Further, one of ordinary skill in the art would recognize how to use sequences to design PCR primers to verify correct gene integration at the chosen locus.

As contemplated herein, the genetically modified or engineered yeast of the present invention includes a functional exogenous invertase expression gene and has a deletion or disruption of the PDC gene. In one embodiment, the genetically modified yeast can include one or more additional exogenous integrated genes other than the integrated functional invertase expression gene. In one embodiment, the genetically modified yeast can include more than one functional invertase expression gene. In another embodiment, the genetically modified yeast can include a functional sucrase gene instead of, or in addition to, the invertase gene. For the purposes of this disclosure, an integrated gene does not include a gene maintained on a plasmid.

Exemplary invertase expression genes suitable for gene integration in a yeast strain include, but are not limited to: an invertase gene from *K. lactis* (KlINV); *S. cerevisiae* (ScSUC2); *Schizosaccharomyces pombe* (invl); and *Aspergillus niger* (invA) also identified as SEQ ID NO: 6; SEQ ID NO: 15; SEQ ID NO: 16; and SEQ ID NO: 17, respectively.

The genetically modified yeast of the present invention can also include exogenous or artificial promoters for the functional exogenous invertase expression gene or any other gene integrated into the yeast. One skilled in the art would know how to select and integrate suitable promoters into the host yeast cell. Examples of suitable promoters include, but are not limited to the promoters for the following *I. orientalis* genes: Pyruvate Decarboxylase (PDC), Glyceraldehyde-3-phosphate dehydrogenase (TDH3), Translational elongation factor (TEF), Transaldolase (TAL), RPL16B, 3-phosphoglycerate kinase (PGK), and Enolase (ENO).

In some embodiments, the integrated functional exogenous invertase expression may be associated with invertase activity which, once integrated into the host yeast cell, can be significantly greater than the desirable or optimal invertase activity. Greater than desired invertase activity can result in a less than optimal fermentation process. Greater than desired invertase activity can be problematic for a host cell and result in a reduction in the sugar consumption rate of the cell. While not wishing to be bound by theory, this reduction in sugar consumption rate can be due to the metabolic burden associated with producing large quantities of invertase protein, or can be due to other reasons that are not well understood.

Accordingly, the present invention also relates to the adjustment of invertase expression associated with the genetically modified yeast. Invertase expression in the genetically modified yeast can be optimized through one or more techniques known in the art. For example, in one embodiment, the amino acid sequence of invertase can be modified to reduce activity. In another embodiment, promoters associated with lower expression of invertase can be identified and integrated into the host yeast. However, the methods and compositions for optimizing invertase expression are not limited to those described herein, and can include any methods or compositions for adjusting or optimizing the invertase expression, as would be understood by a person skilled in the art.

In some embodiments, the yeast can be engineered for improved acetate consumption. Acetate consumption can be improved by overexpression of a gene encoding for an aldehyde dehydrogenase, or an acetyl-CoA synthase. In some embodiments, acetate consumption can be further improved by providing the cell with a greater pool of reducing equivalents to assist in the oxido-reduction of acetate to ethanol. One example of a genetic modification that can increase the pool of reducing equivalents is the deletion or disruption of a gene encoding a glycerol-3-phosphate dehydrogenase (GPD).

In some embodiments, the yeast can include heterologous expression of a transporter that can increase hexose uptake. An example of a transporter than can increase hexose uptake is Hxt1 transporter of *S. cerevisiae*. One skilled in the art would recognize that yeasts are known to have other transporters capable of hexose uptake.

In some embodiments, the genetically engineered yeast of the present invention is capable of manufacturing a fermentation product other than ethanol. In some embodiments, the yeast is capable of producing a fermentation product at a production rate of at least 1.0 grams per liter-hour (g $L^{-1}$ $h^{-1}$), at least 1.5 g $L^{-1}$ $h^{-1}$, or at least 2.0 g $L^{-1}$ $h^{-1}$. In some embodiments, the yeast is capable of producing a fermentation product at a pathway fermentation yield of at least 55 percent, at least 65 percent, at least 70 percent, or at least 75 percent. In some embodiments, the yeast is capable of producing a fermentation product at a final titer of at least 30 g/liter, at least 80 g/liter, or at least 100 g/liter.

As contemplated herein, the genetically engineered yeast is capable of producing a fermentation product using sucrose as a fermentation substrate. The ratio of invertase activity to the rate of glucose consumption via fermentation can be optimized to maximize the manufacture of fermentation product. In some embodiments, the yeast has a ratio of invertase activity to glucose capacity of less than 95, less than 90, less than 80, less than 70, less than 60, less than 50, less than 40, less than 35, less than 30, less than 25 or less than 20. In some embodiments, the yeast has a ratio of invertase activity to glucose capacity of at least 0.95 or at least 10. In some embodiments, the yeast has a ratio of invertase activity to glucose capacity of at least 0.5, 1, 2, 3, 4, 5, 6, 7, 8, 9, 10, 12, 15, or 18. In some embodiments, the yeast has a ratio of invertase activity to glucose capacity in the range of 0.5 to 95, 0.5 to 30, 0.5 to 25, 0.5 to 20, or 1 to 20.

In some embodiments, the invertase activity of the yeast is at least 1, 2, 2.5, 3, 4, 5, 6, 7, 8, or 9 g glucose released/(g CDW*h). In some embodiments, the invertase activity of the yeast is less than 10, 15, 20, 30, 40, or 50 g glucose released/(g CDW*h). In some embodiments, the invertase activity of the yeast is in the range of 1 to 50, 2.5 to 50, 2.5 to 25, 3 to 30, 5 to 30, 3 to 20, or 5 to 20.

The yeast can also be capable of producing a fermentation product using other fermentation substrates in addition to sucrose. In one embodiment, the yeast is capable of using a fermentation substrate that includes sucrose and glucose. In another embodiment, the yeast is capable of using a fermentation substrate that includes sucrose and xylose. In yet another embodiment, the yeast is capable of using a fermentation substrate that includes sucrose, glucose, and xylose. In some embodiments, the yeast is capable of using a fermentation substrate that includes hydrozylates, for example hydrozylates of starch or lignocellulosic hydrozylates. In some embodiments, the yeast is capable of using a fermentation substrate that includes any mixture or combination of sucrose, glucose, fructose, xylose, hydrozylates of starch, or lignocellulosic hydrozylates. As would be understood by a person skilled in the art, the yeast can be used with a fermentation substrate that does not include sucrose.

In one embodiment, the yeast of the present invention can include one or more inducible promoters. For example, the yeast may include a promoter capable of turning off invertase expression after most or all of the sucrose in the fermentation substrate has been hydrolyzed. As a further example, the yeast may contain a promoter that is capable of down regulating after the dissolved oxygen is reduced below a threshold.

Fermentation Processes

The present invention also relates to processes for manufacturing a fermentation product. The fermentation processes includes the step of fermenting a substrate using the genetically engineered yeasts described herein. The fermentation process can also include other steps, as would be understood by a person skilled in the art. Non-limiting examples of additional process steps include maintaining the temperature of the fermentation broth within a predetermined range, adjusting the pH during fermentation, and isolating the fermentation product from the fermentation broth. In some embodiments, the fermentation process is a microaerobic process.

The fermentation processes of the present invention can be run using sucrose as a substrate, as a result of using genetically engineered yeasts having a functional invertase gene. The substrate of the fermentation process can also include other components in addition to sucrose. In one embodiment, the fermentation process substrate can also include glucose, xylose, fructose, hydrozylates of starch, lignocellulosic hydrozylates, or any combination thereof. As contemplated herein, the sucrose component of the substrate will be hydrolyzed into glucose and fructose via the activity of invertase and/or sucrase. Accordingly, in some embodiments, the fermentation substrate may not contain any sucrose because all of the sucrose may be hydrolyzed at some point during the process.

The fermentation process can be run under various conditions. In one embodiment, the fermentation temperature, i.e., the temperature of fermentation broth during processing, is ambient temperature. In some embodiments, the fermentation temperature is maintained within a predetermined range. For example, the fermentation temperature can be maintained in the range of 25 to 45° C., 20 to 40° C., or 33 to 38° C. However, the fermentation temperature is not limited to any specific range recited herein.

The fermentation process can be run within certain oxygen uptake rate (OUR) ranges. In some embodiments, the volumetric OUR of the fermentation process can be in the range of 0.5 to 40, 1 to 30, 3 to 20, or 5 to 16 mmol $O_2$/(L·h). In some embodiments, the specific OUR can be in the range of 0.2 to 13, 0.3 to 10, 1 to 7, or 2 to 6 mmol $O_2$/(g cell dry weight·h). However, the volumetric or specific OURs of the fermentation process are not limited to any specific rates or ranges recited herein.

The fermentation process can be run at various cell concentrations. In some embodiments, the cell dry weight at the end of fermentation can be 1 to 20, 1 to 10, 2 to 8, or 2.5 to 6 g cell dry weight/L. Further, the pitch density or pitching rate of the fermentation process can vary. In some embodiments, the pitch density can be 0.05 to 5, 0.05 to 4, or 0.05 to 2 g cell dry weight/L.

In addition, the fermentation process can be associated with various characteristics, such as, but not limited to, fermentation production rate, pathway fermentation yield, final titer, and the ratio of invertase activity to glucose consumption rate. In some embodiments, these characteristics can be affected based on the selection of the yeast and/or genetic modification of the yeast used in the fermentation process. In some embodiments, these characteristics can be affected by adjusting the fermentation process conditions. In some embodiments, these characteristics can be adjusted via a combination of yeast selection or modification and the selection of fermentation process conditions.

In some embodiments, the fermentation production rate of the process is at least 1.0, at least 1.5, or at least 2.0 g $L^{-1}$ $h^{-1}$. In some embodiments, the pathway fermentation yield of the process is at least 55 percent, at least 65 percent, at least 70 percent, or at least 75 percent. In some embodiments, the final titer of the process is at least 30, at least 80, or at least 100 g/liter. In some embodiments, the process has a ratio of invertase activity to glucose consumption rate of less than 95, less than 90, less than 80, less than 70, less than 60, less than 50, less than 40, less than 35, less than 30, less than 25 or less than 20. In some embodiments, the process has a ratio of invertase activity to glucose consumption rate of at least 0.95 or at least 10. In some embodiments, the process has a ratio of invertase activity to glucose consumption rate of at least 0.5, 1, 2, 3, 4, 5, 6, 7, 8, 9, 10, 12, 15, or 18. In some embodiments, the process has a ratio of invertase activity to glucose consumption rate in the range of 0.5 to 95, 0.5 to 30, 0.5 to 25, 0.5 to 20, or 1 to 20.

In some embodiments, the invertase activity of the process is at least 1, 2, 2.5, 3, 4, 5, 6, 7, 8, or 9 g glucose released/(g CDW*h). In some embodiments, the invertase activity of the process is less than 10, 15, 20, 30, 40, or 50 g glucose released/(g CDW*h). In some embodiments, the invertase activity of the process is in the range of 1 to 50, 2.5 to 50, 2.5 to 25, 3 to 30, 5 to 30, 3 to 20, or 5 to 20.

In some embodiments, the fermentation process can include sucrose as a substrate for only a portion of the process. For example, in one embodiment, the fermentation process can include the step of generating a yeast seed using sucrose as substrate, then running the full production batch with a hydrolysate, a hydrolysate supplemented with sucrose, or other substrate instead of sucrose. In one such embodiment, the fermentation process can be run as a sucrose-fed batch. Further, the fermentation process can be a batch process, continuous process, or semi-continuous process, as would be understood by a person skilled in the art.

Fermentation Products

The genetically engineered yeast of the present invention and the fermentation processes using the genetically engineered yeast can be used to manufacture a variety of compounds. Exemplary fermentation products that can be manufactured using the genetically engineered yeast include, but are not limited to: amino acids, organic acids, hydroxyl-organic acids, alcohols such as butanol, polyols, fatty acids, fatty acids such as methyl esters, monoacyl glycerides, diacyl glycerides, triacyl glycerides, and mixtures thereof. Exemplary organic acids or amino acids include lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof. It is contemplated herein that isolation of the desired fermentation product produced from the fermentation process can be achieved via techniques well known to those skilled in the relevant art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Evaluation Protocols

Strain Capacity Evaluation

The following protocol is used for evaluating the sugar capacity or product capacity of a yeast strain, as defined herein. Fermenters are inoculated with biomass grown in defined medium (adapted from Verduyn, et. al, 1992, Yeast 8, 501-517, see Tables 1, 3, and 4). Seeds are run in 250 mL baffled flasks (50 mL working volume) at 250 rpm and 30° C. The contents of the flasks are harvested at approximately 16-24 hours incubation time. The cell density of the shake flask is measured and a volume of the shake flask broth is selected and inoculated into the fermenter such that the cell dry weight at inoculation is 0.1 g/L. Fermenter initial working volume is 1.5 L. Fermenter media is used as listed in Tables 2, 3, and 4. Sugar is provided by the addition of 140 g/l at the start of the batch (straight batch). pH is started at the ambient pH of the media (4-6) and is controlled at 3.0 with a combination of 28% $NH_4OH$ and 30% $Ca(OH)_2$. 3.8 g per 1.5 L media 28% $NH_4OH$ is used as initial pH control. Once this is exhausted, pH control is switched to $Ca(OH)_2$ for the remainder of the batch. The fermenter systems are sparged at 0.24 slpm with a blend of pure $CO_2$ and air to target 21-23% $CO_2$ in the inlet gas stream. The fermentation is operated such that after the cells achieve a sufficient density, oxygen limitation is achieved and subsequently maintained throughout the rest of the fermentation (e.g., dissolved oxygen less than about 10%). Agitation rate is selected to achieve a peak oxygen uptake rate (OUR) in the fermentation of 21-22 mmol/L·h. The fermentation proceeds until the end of the evaluation which occurs when the sugar is reduced below 2 g/L or until the cessation of product formation, whichever occurs first. Samples are taken immediately after inoculation and at the end of the evaluation. These samples are used for cell dry weight determination as well as HPLC analysis for determination of sugar and product concentrations.

Invertase Activity Evaluation

The capability of a cell to convert sucrose to glucose and fructose is evaluated by the following protocol. The strains are taken from a fresh YPD plate and used to inoculate 50 mL of YPD liquid media. The culture is allowed to grow at 30° C./250 rpm overnight (16 hours). Fresh cultures are inoculated to an $OD_{600}=1.0$ in 50 mL of YPD liquid media and allowed to grow at 30° C./250 rpm for 3 hours. The cells are harvested by centrifugation at 3,500 rpm for 4 minutes. The pellets are washed with 25 mL of water and centrifuged at 3,500 rpm for 4 minutes; this step is repeated 2 times. Washed cells are resuspended in 5 mL of water. 10 µL of cell suspension is incubated with 40 µL water, 250 µL of 0.2 M sodium acetate, pH 4.9 and 125 µL of 0.5 M sucrose for 10 min at 37° C. Samples are filtered through a 0.22 µm filter. The glucose released is immediately measured on a YSI2950 (Xylem Inc.). The activity is expressed as grams of glucose released per gram of cell dry weight/hour. Assays are carried out in duplicate.

This assay is adapted from Silveira, M. C. F., Carvajal, E., Bon, E. P. S., Assay for in vivo yeast invertase activity using NaF (1996) Analytical Biochemistry, 238 (1), pp. 26-28, and Georis, I., Cassart, J.-P., Breunig, K. D., Vandenhaute, Glucose repression of the *Kluyveromyces lactis* invertase gene KIINV1 does not require Mig1p (1999), Molecular and General Genetics 261(4-5):862-70.

Example 1

Genetically Modified Yeast Strains

Strain 1-1

Strain P-8b described by Rush et al. (Int'l. App. No. PCT/US2013/052069) is an evolved Issachenkia *orientalis* host strain in which both alleles of the URA3, PDC and GPD genes are deleted followed by the addition of diploid alleles of the following genes under control of heterologous promoters: *I. orientalis* PYC1, *Schizosaccharomyces pombe* MAE, *Leshmania mexicana* FRD, *Rhizopus delemar* MDH, and *I. orientalis* FUM (SEQ ID NO: 4). Strain 1-1 is created using the methods to create strain P-8b with the following change: 1) In Strain 1-1, the *L. mexicana* FRD gene of P-8b is replaced with the variant of the *L. mexicana* FRD gene of SEQ ID NO: 3.

Strain 1-1a

Strain 1-1 is grown for several rounds on 5-fluoroorotic acid (FOA) plates to identify a strain in which the URA3 marker has looped out. Resulting isolates are streaked for single colony isolation on YPD plates. A single colony is selected. Loss of the URA3 marker is verified by PCR. A PCR verified isolate is designated Strain 1-1a.

Strain 1-2

Strain 1-1a is transformed with SEQ ID NO: 5. SEQ ID NO: 5 contains: i) an expression cassette for the selectable marker gene URA from *I. orientalis* (IoURA) including a repeated portion of the URA promoter; ii) an expression cassette for an invertase from *K. lactis* (KIINV), encoding the amino acid sequence SEQ ID NO: 6 expressed by the PDC promoter SEQ ID NO: 7; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 5 into the selected colony is verified by PCR. A PCR verified isolate is designated Strain 1-2.

Strain 1-3

Strain 1-1a is transformed with SEQ ID NO: 8. SEQ ID NO: 8 contains: i) an expression cassette for the selectable marker gene URA from *I. orientalis* (IoURA) including a repeated portion of the URA promoter; ii) an expression cassette for an invertase from *K. lactis* (KIINV), encoding the amino acid sequence SEQ ID NO: 6 expressed by the TAL promoter SEQ ID NO: 9; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 8 into the selected colony is verified by PCR. A PCR verified isolate is designated Strain 1-3.

Strain 1-4

Strain 1-1a is transformed with SEQ ID NO: 10. SEQ ID NO: 10 contains: i) an expression cassette for the selectable marker gene URA from *I. orientalis* (IoURA) including a repeated portion of the URA promoter; ii) an expression cassette for an invertase from *K. lactis* (KIINV), encoding the amino acid sequence SEQ ID NO: 6 expressed by the RPL16B promoter SEQ ID NO: 11; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 10 into the selected colony is verified by PCR. A PCR verified isolate is designated Strain 1-4.

Strain 1-5

Strain P-8b as described in the section titled "Strain 1-1" above is co-transformed with the integration fragments 6-1 and 6-2 listed in the second column of Table 3 in Rush et al. (Int'l. App. No. PCT/US2013/052069). Integration fragments 6-1 and 6-2 target the *E. coli* transhydrogenase gene to the GPD locus. Successful integrants in each case are identified as blue colonies on selection plates with 5-bromo-4-chloro-3-indolyl-alpha-D-galactopyranoside and lacking uracil, and confirmed by PCR. A PCR verified isolate is designated Strain 1-5.

Strain 1-6

Strain 1-5 is transformed with the plasmid of SEQ ID NO: 12. SEQ ID NO: 12 contains: i) an expression cassette for the selectable marker gene invertase from *S. cerevisiae* (ScSUC2); and ii) an expression cassette for CRE recombinase gene (Cre) to recycle the selectable markers ScMEL5 & IoCYB2A. Transformants are selected on YNB plates containing 2% sucrose as sole carbon source and 32 µg/mL x-alpha-gal which provides colorimetric indication of the absence of the ScMEL5 marker gene. Resulting transformants are streaked for single colony isolation on YPD containing 32 µg/mL x-alpha-gal. A single white colony is selected. Loss of ScMEL5 and IoCYB2A from the selected white colony is verified by PCR. A PCR verified isolate is designated Strain 1-5a.

Strain 1-5a is grown for several rounds on 5-fluoroorotic acid (FOA) plates to identify a strain in which the URA3 marker has looped out. Resulting isolates are streaked for single colony isolation on YPD plates. A single colony is selected. Loss of the URA3 marker is verified by PCR. A PCR verified isolate is designated Strain 1-6.

Strain 1-7

Strain 1-6 is transformed with SEQ ID NO: 10. SEQ ID NO: 10 contains: i) an expression cassette for the selectable marker gene URA from *I. orientalis* (IoURA) including a repeated portion of the URA promoter; ii) an expression cassette for an invertase from *K. lactis* (KIINV), encoding the amino acid sequence SEQ ID NO: 6 expressed by the RPL16B promoter SEQ ID NO: 11; and iii) flanking DNA for targeted chromosomal integration into integration locus A. Transformants are selected on ScD-Uracil plates. Resulting transformants are streaked for single colony isolation on ScD-Uracil plates. A single colony is selected. Correct integration of SEQ ID NO: 10 into the selected colony is verified by PCR. A PCR verified isolate is designated Strain 1-7.

Strain 1-8

Strain 1-7 is transformed with SEQ ID NO: 13. SEQ ID NO: 13 contains: i) an expression cassette for the selectable marker gene melibiase from S. cerevisiae (ScMEL5) flanked by LoxP sites; ii) an expression cassette for an invertase from K. lactis (KlINV), encoding the amino acid sequence SEQ ID NO: 6 expressed by the RPL16B promoter SEQ ID NO: 11; and iii) flanking DNA for targeted chromosomal integration into integration locus A. Transformants are selected on YNB plates containing 2% melibiose as sole carbon source and 32 ag/mL x-alpha-gal which provides colorimetric indication of the presence of the ScMEL5 marker gene. Resulting transformants are streaked for single colony isolation on YPD containing 32 µg/mL x-alpha-gal. A single blue colony is selected. Correct integration of SEQ ID NO: 13 into the selected blue colony is verified by PCR. A PCR verified isolate is designated Strain 1-8.

Example 2

Fermentation Using Genetically Modified Yeast Strains

This Example demonstrates the capability of the recombinant yeast strains having an exogenous invertase activity gene described above to convert sucrose to glucose and fructose, and subsequently and/or concurrently convert glucose to a fermentation product such as succinic acid.

Fermentation Conditions for Strains 1-1, 1-2, 1-3, and 1-4

The yeast strains 1-1, 1-2, 1-3, and 1-4, are run in fermenters to test succinic acid production. Fermenters are inoculated with biomass grown in defined medium (adapted from Verduyn, et. al, 1992, Yeast 8, 501-517, see Tables 1, 3, and 4). Seeds are run in 250 mL baffled flasks (50 mL working volume) at 250 rpm and 30° C. The contents of the flasks are harvested at approximately 16-24 hours incubation time with 10% v/v inoculum used to start fermenters. Fermenter initial working volume is 1.5 L. The cell dry weight at inoculation is found in Table 5. Fermenter media is outlined in Tables 2, 3, and 4. Glucose or sucrose is added to achieve a concentration of 140 g/L at the start of the batch (straight batch). pH is started at the ambient pH of the media (4-6) and is allowed to drop to pH 3.0, after which it is controlled at 3.0 for the remainder of the batch with a combination of 28% $NH_4OH$ and 30% $Ca(OH)_2$. 3.8 g per 1.5 L media 28% $NH_4OH$ is used as initial pH control. Once this is exhausted, pH control is switched to $Ca(OH)_2$ for the remainder of the batch. The fermenter systems are sparged at 0.24 slpm with a blend of pure $CO_2$ and air to target 21-23% $CO_2$ in the inlet gas stream. These fermentations are operated such that after the cells achieve a sufficient density, oxygen limitation is achieved and subsequently maintained throughout the rest of the fermentation (e.g., dissolved oxygen less than about 10%). Agitation rate is selected to achieve a peak oxygen uptake rate (OUR) in the fermentations target 21-22 mmol/L-h.

Fermentation Conditions for Strains 1-5 and 1-8

The yeast strains 1-5 and 1-8 are run in fermenters to test succinic acid production. Fermenters are inoculated with biomass grown in defined medium (adapted from Verduyn, et. al, 1992, Yeast 8, 501-517, see Tables 1, 3, and 4). Seeds are run in 250 mL baffled flasks (50 mL working volume) at 250 rpm and 30° C. The contents of the flasks are harvested at approximately 16-24 hours incubation time with 2.5% v/v inoculum used to start fermenters. Fermenter initial working volume is 1.25 L. The cell dry weight at inoculation is found in Table 5. Fermenter media is outlined in Tables 2, 3, and 4. Carbon substrate (glucose or sucrose) is provided by the addition of 140 g/L at the start of the batch. pH is started at the ambient pH of the media (pH 4-6) and controlled at 3.5 using 28% $NH_4OH$ until 5 mL of ammonium hydroxide solution is added to the 1.25 L batch. At this point, pH control is switched to $Ca(OH)_2$. 1.5 g of calcium hydroxide per 100 mL deionized water is used. Once the 100 mL calcium hydroxide is exhausted pH is allowed to freefall. The fermenter systems are sparged at 0.125 slpm with air targeting 0.125 slpm aeration. Agitation rate is maintained to achieve an oxygen uptake rate of the yeast from 13-22 mmol/L-h. These fermentations are operated such that after the cells achieve a sufficient density, oxygen limitation is achieved and subsequently maintained throughout the rest of the fermentation (e.g., dissolved oxygen less than about 10%).

Dissolved oxygen is measured using Mettler Toledo INPRO® 6800 sensor (Mettler-Toledo GmbH, Urdorf, Switzerland), calibrated prior to inoculation. 0% is calibrated by sparging nitrogen, 100% is calibrated using the run conditions in the vessel as detailed above (prior to inoculation).

TABLE 1

Defined Media for Seed Flask Cultures

| Chemicals | g/L or mL added |
|---|---|
| Ammonium Sulfate | 5.0 g/L |
| Magnesium sulfate heptahydrate | 0.5 g/L |
| Potassium phosphate monobasic (MKP) | 3.0 g/L |
| Glucose | 100.0 g/L |
| Trace solution | 1.0 mL |
| Vitamin solution | 1.0 mL |
| MES buffer (0.1M) | 19.0 g/L |
| Glycerol (10% stock) | 1.0 mL |
| De-ionized Water | 868 g |

TABLE 2

Defined Media for Fermenters

| Compound | Concentration (g/kg) |
|---|---|
| $C_6H_{12}O_6$ or Sucrose | 140 |
| $(NH_4)_2SO_4$ | 0.2 |
| $KH_2PO_4$ | 0.5 |
| $MgSO_4$—$7H_2O$ | 0.125 |
| Biotin Stock solution (mL) | 5 |
| 1000x Trace Solution (mL) | 1 |

TABLE 3

Trace Element 1000x Stock Solution.

| Chemical | g/1.0 L |
|---|---|
| $ZnSO_4 \cdot 7H_2O$ | 4.50 |
| $MnCl_2 \cdot 2H_2O$ | 0.84 |
| $CuSO_4 \cdot 5H_2O$ | 0.30 |
| $FeSO_4 \cdot 7H_2O$ | 3.00 |

TABLE 4

Vitamin 1000x Stock Solution

| Chemical | g/1.0 L |
|---|---|
| Biotin (D−) | 0.05 |

Cell concentration is obtained from an optical density measurement using an established conversion factor between dry cell mass and optical density. Optical density is measured at wavelength of 600 nm with a 1 cm pathlength using a model Genesys20 spectrophotometer (Thermo Scientific). Unless explicitly noted otherwise, an experimentally derived conversion factor of 1.51 $OD_{600}$ units per 1 g dry cell mass is used to estimate cell dry weight ("CDW").

Oxygen uptake rate ("OUR") is calculated using methods known to those in the art as described above. For this example, Oxygen and $CO_2$ values are measured by an EGAS L instrument (Sartorious). While a mass spectrometer is not necessarily used, the results obtained by the EGAS L are expected to be substantially the same. Nitrogen value is calculated as 100% less % measured $CO_2$ minus, less % measured Oxygen. Samples are taken at whichever occurred first, 57 h batch time or the reduction of total carbon sources (glucose, fructose and/or sucrose) to <10 g/L (e.g., some batches can be sampled as soon at 33 h if the carbon sources are sufficiently exhausted at this time) and analyzed for biomass growth via $OD_{600}$, succinate and glucose by high performance liquid chromatography with refractive index and ultraviolet detector.

TABLE 5

Cell Dry Weight at the beginning and end of fermentation.

| Strain | Initial CDW (g/L) | Final CDW (g/L) |
|---|---|---|
| 1-1 | 0.1 | 6 |
| 1-2 | 0.1 | 5.9 |
| 1-3 | 0.1 | 5.5 |
| 1-4 | 0.1 | 6.8 |
| 1-5 | 0.2 | 5.7 |
| 1-8 | 0.1 | 5.2 |

Figure 3:
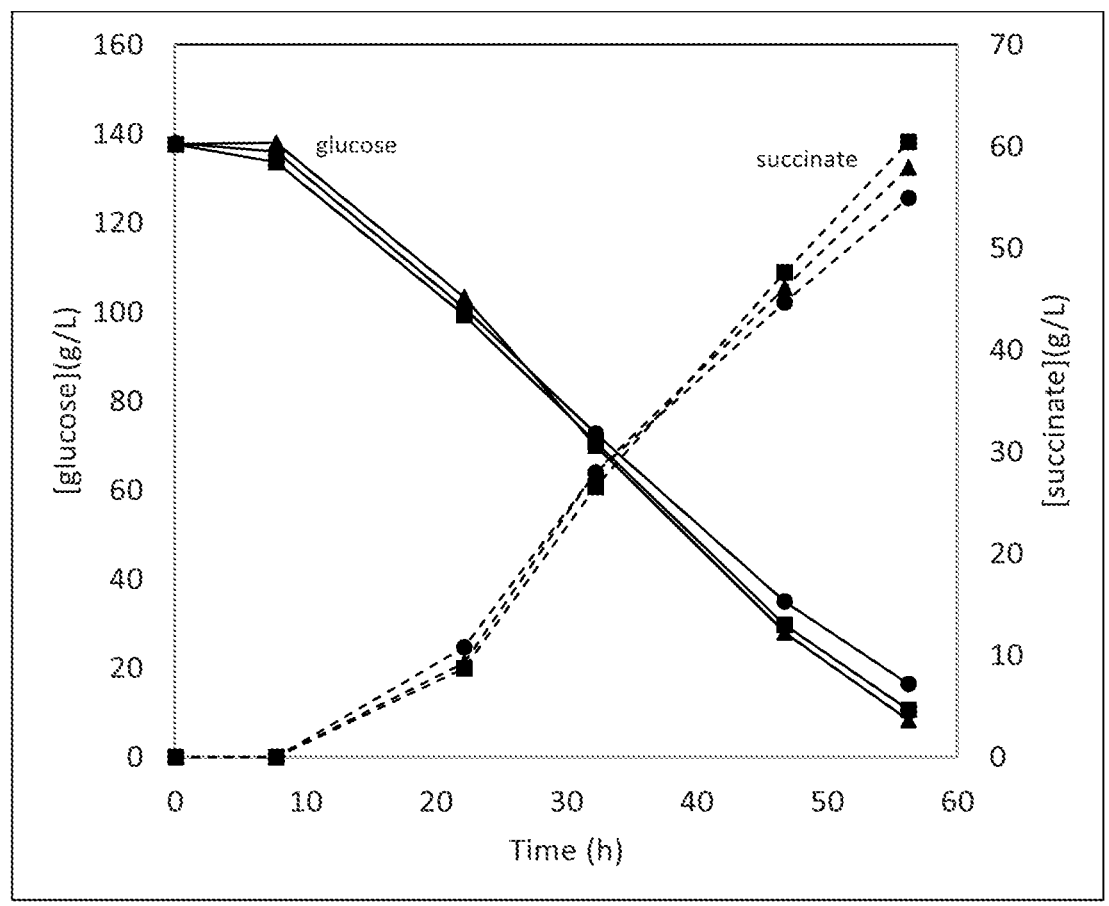
FIG. 3 is a graph showing glucose (solid lines) and succinate (dashed lines) titer for an exemplary fermentation process using strain 1-1 (squares), strain 1-2 (circles) and strain 1-4 (triangles)

Table 6 illustrates that a strain with a "ratio of invertase activity to glucose capacity" that is significantly less than 95 produces more succinate than a strain with a "ratio of invertase activity to glucose capacity" that is greater than 95. Accordingly, a strain having a relatively weak promoter of the invertase gene can produce more succinate than a comparable strain having a strong promoter (see also FIG. 3).

TABLE 6

Glucose consumption, invertase activity, and product formation for selected strains

| Strain | Batch finish time (h) | Glucose Consumption Rate (g/(L* h)) | Glucose capacity (g/(g CDW * h)) | Succinate Rate (g/(L* h)) | Succinate Titer (g/L) | Succinate Yield (g/g) | Succinate Specific Rate (g/(g CDW * h)) | Invertase Activity (g glucose released/(g CDW *h)) | Ratio of invertase activity to glucose capacity (g glucose released/(g cell dry weight * hour))/(g glucose consumed/(g cell dry weight * hour)). |
|---|---|---|---|---|---|---|---|---|---|
| 1-1 | 56.2 | 2.25 | 0.51 | 1.12 | 60.5 | 0.497 | 0.26 | No invertase present | No invertase present |
| 1-2 | 56.2 | 2.15 | 0.55 | 1.02 | 54.9 | 0.473 | 0.26 | 53.97 | 98.13 |
| 1-3 | 56.2 | 2.27 | 0.56 | 1.07 | 57.6 | 0.469 | 0.26 | NM | NM |
| 1-4 | 56.2 | 2.29 | 0.54 | 1.10 | 57.9 | 0.480 | 0.26 | 9.87 | 18.28 |

NM = not measured

Figure 2:
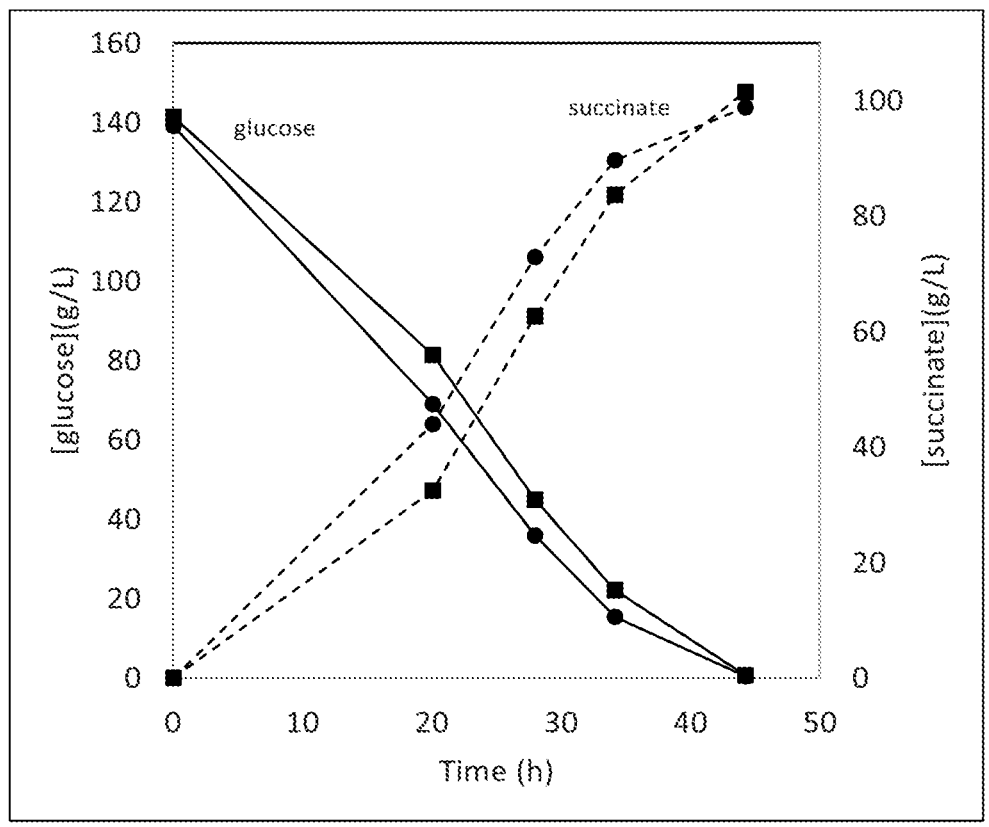
FIG. 2 is a graph showing glucose (solid lines) and succinate (dashed lines) titer for exemplary fermentation processes using strain 1-5 (circles) and strain 1-8 (squares).

Table 7 illustrates that a strain expressing an invertase gene having the same promoter as strain 1-4 in either a glucose or a sucrose fermentation can achieve a succinate titer equivalent to an equivalent comparable strain without an invertase gene in a glucose fermentation. FIGS. 1 and 2 also show data supporting this conclusion.

TABLE 7

Succinate titers for glucose and sucrose fermentations of selected strains

| Strain | Batch finish time | Sugar provided to fermentation | Sugar Consumption Rate (g/(L* h)) | Sugar Specific Consumption Rate (g/(g CDW * h)) | Product Rate (g/(L* h)) | Product Titer (g/L) | Product Yield (g/g) | Product Specific Rate (g/(g CDW * h)) |
|---|---|---|---|---|---|---|---|---|
| 1-5 | 43.8 | Glucose | 3.17 | 0.76 | 2.44 | 98.8 | 0.770 | 0.58 |
| 1-8 | 44.2 | Glucose | 3.18 | 0.77 | 2.48 | 101.5 | 0.779 | 0.6 |
| 1-8 | 44.2 | Sucrose | 3.05 | 0.69 | 2.43 | 99.5 | 0.799 | 0.55 |

The invention claimed is:

1. A genetically engineered yeast capable of manufacturing a fermentation product, comprising: a yeast capable of producing a fermentation product at a fermentation production rate of at least 1.0 g $L^{-1}h^{-1}$, wherein the genetically engineered yeast is a modified *Issatchenkia orientalis* yeast; has a functional invertase gene; and has a deletion or disruption of the pyruvate decarboxylase (PDC) gene.

2. The yeast of claim 1, wherein the yeast is capable of a fermentation production rate of at least 1.5 g $L^{-1}h^{-1}$.

3. The yeast of claim 1, wherein the yeast is capable of a fermentation production rate of at least 2.0 g $L^{-1}h^{-1}$.

4. The yeast of claim 1, wherein the yeast is capable of producing a fermentation product at a pathway fermentation yield of at least 55 percent.

5. The yeast of claim 1, wherein the yeast is capable of producing a fermentation product at a pathway fermentation yield of at least 65 percent.

6. The yeast of claim 1, wherein the yeast is capable of producing a fermentation product at a pathway fermentation yield of at least 70 percent.

7. The yeast of claim 1, wherein the yeast is capable of producing a fermentation product at a pathway fermentation yield of at least 75 percent.

8. The yeast of claim 1, wherein the yeast is capable of producing a fermentation product at a final titer of at least 30 g/liter.

9. The yeast of claim 1, wherein the yeast is capable of producing a fermentation product at a final titer of at least 80 g/liter.

10. The yeast of claim 1, wherein the yeast has a ratio of invertase activity to glucose capacity of less than 95.

11. The yeast of claim 1, wherein the yeast has a ratio of invertase activity to glucose capacity of less than 30.

12. The yeast of claim 1, wherein the yeast has a ratio of invertase activity to glucose capacity of less than 20.

13. The yeast of claim 1, wherein the yeast has a ratio of invertase activity to glucose capacity of at least 0.95.

14. The yeast of claim 1, wherein the yeast has a ratio of invertase activity to glucose capacity of at least 10.

15. The yeast of claim 1, wherein the yeast is Crabtree-negative.

16. The yeast of claim 1, wherein the functional invertase gene is selected from the group consisting of SEQ ID NO: 6; SEQ ID NO: 15; SEQ ID NO: 16; and SEQ ID NO: 17.

17. The yeast of claim 1, further comprising an exogenous or artificial promoter for the functional invertase gene.

18. The yeast of claim 17, wherein the promoter is selected from the group consisting of Pyruvate decarboxylase, Glyceraldehyde-3-phosphate dehydrogenase, Translational elongation factor, Transaldolase, RPL16B, 3-phosphoglycerate kinase, and Enolase.

19. The yeast of claim 1, wherein the yeast is capable of manufacturing a fermentation product selected from the group consisting of: lactic acid, citric acid, malonic acid, hydroxy butyric acid, adipic acid, lysine, keto-glutaric acid, glutaric acid, 3-hydroxy-proprionic acid, succinic acid, malic acid, fumaric acid, itaconic acid, muconic acid, methacrylic acid, and acetic acid and derivatives thereof and salts thereof.

\* \* \* \* \*

SEQUENCE LISTING

<160> NUMBER OF SEQ ID NOS: 17

<210> SEQ ID NO 1
<211> LENGTH: 993
<212> TYPE: DNA
<213> ORGANISM: Issatchenkia orientalis

<400> SEQUENCE: 1

```
aacagtatcg atgaaaggtg tacgactta taagagggct tttctcgtag ctctttcaaa      60
tagtatctca ttgtatacta agatagtttg tatttgtgtg tgtgtgtcag tgtaagtgtt    120
agtatacttg ttttcctctt tcccctagag ttggtggtgt gttttgttgg aacgtacatt    180
agatgcataa tgcgtgacac cgccatgatg gttgtattct accaatgaga catggccgtt    240
gatcctgctg tgtgggtcat gagacatcac ctcttggggg ggattctcct ataattggca    300
ccgtgtatgc ctcaaccact aacttccacc ctataactga atatattaca taagcaaatc    360
tactttttgt ttgtgttgat cgccatcgtt gaaattcgcg caacttctgg tggctcaacg    420
ctgctgttct atcggtatcc taagagatgt ctttgccctg agtctagggt aaactatcca    480
ccttcgttgc tgtttgacta dacagctact aactttaggt tagtaaatga ataacggctc    540
gctctcatga tcacttctct acatcaccct aacaagtgta ttattttttt ttcaagtggg    600
tgttgctgtt ggtgctagcc ttagtgccct cgttaatagt tgaacaaaca ctggcatttg    660
gagtataatg aaaagggatc actaccccc gcttcctgtt ccgcttctcc cttccggaaa     720
aaccacccac cctttctttt cccccactaa tgtatgaatt tttccgttcc caggggaatg    780
gcccacttgg ttctctgtta acccacacaa ttttgacgca tcccacacac cttttttttt    840
tctaccccac acttttccctt gaaaaatctc caatttgaac tggcaatttt cacccccac    900
cacttgcatt cattagtgag tcaatccatc ccgcggtcgg agattcggaa tccacctact    960
ggtaatctgt aatctatatt cccgctgacc ctt                                993
```

<210> SEQ ID NO 2
<211> LENGTH: 690
<212> TYPE: DNA
<213> ORGANISM: Issatchenkia orientalis

<400> SEQUENCE: 2

```
tagatactgc tcctcctcca atcgaattat tagctgaaac tgttccaact ttgaagagat      60
tgggtaaatt aagaccagat tttgaaattt taattgacgg tggtgtcaaa agaggtaccg    120
atattttgaa agcagtcgca atcggtggcc aagatgtcag agtttcagtt ggtatgggta    180
gacctttctt atatgccaac tcttgctatg gtgaagcagg tgttagaaaa ttaattcaaa    240
atctaaagga tgaattagaa atggatatga gattgttggg tgtcactaaa atggaccagc    300
tatcttcgaa acatgtcgat actaaacgtt tgattggtag agatgcgatc aactatttgt    360
atgataatgt atacagccca atcgaaaccg ttaaattcaa caatgaagat tgattgttgg    420
aaatatatta ttcataaagg cgaaaacatt cccttggtat tttattccaa atttatgata    480
catagacgta ttttttatat ataagttat attattaatg attcaagaaa aagttcaaat    540
aaactaatgg atcaacctat ttcgacccctt tcttcattgc tacttcttcc ttaagcaaca    600
```

```
gatgattaag tagatactgt tttttttagcc aatagtatct cgccgaggag ttatacttga    660
ctagctcttg ctcaagaatc ttcctaagac                                      690

<210> SEQ ID NO 3
<211> LENGTH: 3435
<212> TYPE: DNA
<213> ORGANISM: Artificial Sequence
<220> FEATURE:
<223> OTHER INFORMATION: FRD variant

<400> SEQUENCE: 3
atggctgatg gcaaaacctc tgcatcagtt gttgctgttg atgctgaacg tgccgctaag      60
gaaagagatg cagcagctag agctatgttg caaggtggtg gtgtctctcc tgctggcaag     120
gcacaattgt tgaaaaaggg tttggttcac actgttccat ataccttaaa ggttgtcgtc     180
gcagatccaa aggaaatgga aaggcaact gctgacgcag aagaggtttt acaagctgca      240
tttcaagtcg tcgacaccct tttgaacaac tttaacgaaa actcagaagt ttcaagagtc     300
aataggttgg cagttggtga ggaacatcaa atgtctgaaa cattgaaaca cgtcatggcc     360
tgttgtcaaa aggtttatca ttcctccaga ggtgttttg acccagcagt tggtccatta      420
gtccgtgaac ttagagaagc tgctcacaag ggtaaaactg ttccagccga aagagttaat     480
gatttgttat ccaaatgtac ccttaatgca tcttttttcaa ttgatatgtc cagaggtatg    540
attgcaagga agcatccaga cgccatgttg gatttgggtg gtgtcaacaa gggttatggt     600
atcgactaca ttgttgaaca cttaaactct ttgggttatg atgatgtctt tttcgaatgg     660
ggtggtgatg ttagagcatc cggcaaaaac cagttatctc aaccttgggc tgttggtatt    720
gttagaccac ctgccttggc cgacattaga actgttgtcc cagaggacaa aagatccttt     780
atccgtgtcg tcagattgaa caacgaagct attgctacct ctggtgatta tgagaatttg     840
gttgaaggtc ctggttctaa ggtttactct tccaccttca atccaacttc caaaaacttg     900
ttggaaccta ccgaagcagg tatggctcaa gtttctgtca agtgttgctc atgtatctac     960
gctgatgctt tagcaacagc agctttgttg aaaaacgatc ctgctgccgt tagaaggatc    1020
ttagataact ggagatatgt cagagatact gttactgact acaccactta cacaagggaa    1080
ggtgaaagag ttgctaagat gttggaaatt gctaccgaag atgctgaaat gagagcaaag    1140
agaatcaagg ctctctttac cagcaagagtt atcattgttg gtggtggttt ggccggttgt    1200
tccgcagcta tcgaagcagc taactgtggc gcccacgtca tcttgttagc aaaggaacca    1260
aagttaggtg gtaactctgc aaaggctacc tccggtatca acgcctgggg tactagagca    1320
caagcaaaac aaggtgtcat ggacggcggc aagttttcg aaagagatac ccatagatcc    1380
ggcaagggtg gtaattgcga tccatgcctt gttaagactt tgtccgttaa gtcctctgat    1440
gcagttaagt ggttatctga attaggtgtt ccattgactg ttttgtctca attaggtggt    1500
gcttcaagga acgttgtca ccgtgcacca gataagtctg atggtacacc agtcccagtt    1560
ggtttcacca ttatgaaaac ccttgaaaac cacattgtca acgatttgtc cagacatgtt    1620
acagttatga caggtattac cgtcacagct ttagaatcta catcaagagt cagacctgat    1680
ggtgttttag tcaagcatgt tactggtgtt cacttgattc aggcatctgg tcaatctatg    1740
gttttgaatg cagacgctgt tatcttagct actggtggtt tctccaatga tcataccccca    1800 aactcccttt tacaacaata cgcccccacag ttgtcatctt ttccaacaac caatggtgtc    1860
tgggcaactg gcgatggtgt taagatggct tccaagttgg gtgtcgcct agttgatatg    1920 gataaggtcc aattacatcc taccggcttg ttagacccaa aagatccatc taatagaacc    1980
```

```
aagtatcttg gtccagaggc cttaagaggt tccggcggtg tcttgttaaa caaaaacggt    2040
gaaagatttg ttaatgaatt agacttaaga tctgttgtct ctcaagctat catcgcacaa    2100
gataatgagt acccaggctc tggtggttcc aagttcgcat actgtgtttt gaacgaaact    2160
gcagcaaagt tattcggcaa aaacttcctt ggtttctact ggaatagatt aggtcttttc    2220
caaaaggttg attccgttgc tggtttagct aagttgattg ttgtccaga agctaatgtt    2280 gttgctacat tgaagcaata tgaggagtta tcttccaaaa agcttaatcc ttgtccattg    2340
actggcaagt ctgtctttcc ttgtgtttta ggcactcaag gtccatacta tgttgccttg    2400
gttaccccat ccattcacta cactatgggg ggttgtttga tttccccatc tgctgagatg    2460
caaaccattg acaactctgg tgttactcct gtcagacgtc caatcttagg cttattcggt    2520
gctggtgaag ttactggcgg tgtccatggt ggtaacagat taggcggtaa ctctttgtta    2580
gaatgtgttg ttttcggcaa gatcgctggt gacagagctg caaccatctt gcaaaagaaa    2640
aacaccggct tatcaatgac agaatggtct actgtcgtct taagagaagt tagagaaggt    2700
ggtgtctatg gtgctggttc cagagttttg aggtttaaca tgcctggtgc attacagaga    2760
actggtttag cttaggtca attcatcggt atcagaggtg attgggacgg tcacagattg    2820
atcggttact attctccaat cactttacct gatgatgttg gtgttattgg tatcttagct    2880
agagcagaca agggtagatt ggcagaatgg atttctgcat tgcagccagg tgacgctgtt    2940
gagatgaagg cctgcggtgg tcttatcatt gacagaagat cgctgaaag acatttcttt    3000 ttccgtggtc ataagatcag aaagttggcc cttatcggtg gtggtactgg tgttgcacca    3060
atgttacaaa tcgtcagagc tgctgtcaaa aagccatttg tcgattcaat tgagtccatt    3120
cagttcatct atgctgcaga ggatgttcc gagcttacat acagaacctt acttgaatct    3180
tacgaagagg aatatggttc agaaaagttt aagtgtcact tcgtttttgaa taacccacca    3240 gctcaatgga ctgacggtgt tggttttcgtt gatactgcat tgttgagatc cgcagttcaa    3300
gcaccatcaa atgatttgct tgttgcaatt tgtggtccac caatcatgca aagagcagtt    3360
aagggtgcat tgaaaggttt aggttacaat atgaatcttg ttagaaccgt tgacgaaact    3420
gaaccaccat cataa                                                     3435

<210> SEQ ID NO 4
<211> LENGTH: 1458
<212> TYPE: DNA
<213> ORGANISM: Issatchenkia orientalis

<400> SEQUENCE: 4
atgttagctg ctagatcatt aaaggcaaga atgtcaacaa gagctttctc aactacctca     60
attgcaaaaa gaatcgaaaa agatgcattt ggtgacattg aagtcccaaa tgagaaatat    120
tggggtgctc aaactcaaag atctttacaa aatttcaaaa ttggtggtaa gagagaagtt    180
atgccagaac caatcatcaa atcttttggt attttaaaga aggctactgc taagatcaat    240
gctgagtctg gtgctttaga cccaaagtta tctgaagcca tccaacaagc tgcaaccgaa    300
gtttatgaag gtaaactaat ggaccatttc ccattagttg tctttcaaac cggttctggt    360
actcaatcta acatgaatgc caatgaagtc atctctaata gagcaattga atcttgggt    420 ggtgaattag ctctaaaac tccagtccat cctaatgatc atgttaatat gtcccaatct    480
tctaatgata ctttccctac tgtcatgcat attgcagcag ttacagaagt ttcatcccat    540
ttattaccag aattaactgc actaagagat gcattgcaaa agaaatccga tgaatttaag    600
```

```
aatattatca aaatcggtag aacccattta caagatgcaa ctcctttaac tttaggtcaa    660
gaattttctg gttatgttca acaatgtact aatggtatca aaagaatcga aattgctctt    720
gaacatttga gatacttagc tcaaggtggt actgccgttg gtactggtct aacaccaag    780 aaaggttttg ctgaaaaggt tgcaaatgaa gtcactaaat tgactggttt acaattctat    840
accgctccaa ataaattcga agcccttgca gctcacgatg ctgttgttga aatgtctggt    900
gctttgaata ccgttgcagt ctcattattc aaaatcgctc aagatatcag atatttgggt    960
tccggcccaa gatgtggtta tggtgaattg gctttaccag aaaatgaacc aggttcttcc   1020
atcatgccgg gtaaagttaa cccaactcaa acgaagcttt gactatgct ttgtacccaa    1080 gtctttggta accactcttg tattacccttt gcaggtgctt caggtcaatt cgaattgaat   1140
gtctttaagc cagttatgat ctccaacttg ttatcttcta ttaggttatt aggtgatggt   1200
tgtaattctt ttagaatcca ctgtgttgaa ggtatcattg caaataccga caagattgat   1260
aaattactac atgaatctct catgttagtt actgctttga acccacacat tggttacgat   1320
aaggcttcca agattgcaaa gaatgcacac aagaagggct tgacattgaa acaatctgca   1380
ttggaattag gttacttgac cgaagaacaa ttcaatgaat gggttagacc agaaaacatg   1440
attggtccaa aggattaa                                                  1458

<210> SEQ ID NO 5
<211> LENGTH: 5797
<212> TYPE: DNA
<213> ORGANISM: Artificial Sequence
<220> FEATURE:
<223> OTHER INFORMATION: URA3-invertase-locus A transformation sequence

<400> SEQUENCE: 5
aaaccataat gcgtgacacc gccatgatgg ttgtattcta ccaatgagac atggccgctg     60
atcctgttgt gtgggtcatg ggacatcacc tcttgggggg gattctccta taattggcac    120
cgtgtatgcc tcaaccacta acttccaccc tataactgaa tatattacat aagcaaatct    180 acttttgtt tgtgttgatc gccatcgttg aaattcgcgc aacttctggt ggctcaacgc    240
tgctgttcta tcggtatcct aagagatgtc tttgccctga gtctagggta aactatccac    300
cttcgttgct gtttgactag acagctacta actttacggt agtaaatgaa taacggctcg    360
ctctcatgat cacttctcta catcacccta acaagtgtat tatttttttt tcaggtgggt    420
gttgctgttg gtgctagcat atggcggccg cggatccctc gaggagtcca tcggttcctg    480
tcagatggga tactcttgac gtggaaaatt caaacagaaa aaaaacccca ataatgaaaa    540
ataacactac gttatatccg tggtatcctc tatcgtatcg tatcgtagcg tatcgtagcg    600
taccgtatca cagtatagtc taatattccg tatcttattg tatcctatcc tattcgatcc    660
tattgtattt cagtgcacca ttttaatttc tattgctata atgtccttat tagttgccac    720
tgtgaggtga ccaatggacg agggcgagcc gttcagaagc gcgaagggt gttcttccca    780 tgaatttctt aaggagggcg gctcagctcc gagagtgagg cgagacgtct cggtcagcgt    840 atccccttc ctcggctttt acaaatgatg cgctcttaat agtgtgtcgt tatcctttg    900 gcattgacgg gggagggaaa ttgattgagc gcatccatat ttttgcggac tgctgaggac    960
aatggtggtt tttccgggtg gcgtgggcta caaatgatac gatggttttt ttcttttcgg   1020
agaaggcgta taaaaggac acggagaacc catttattct aaaaacagtt gagcttcttt    1080
aattattttt tgatataata ttctattatt atatattttc ttcccaataa acaaaataa    1140 aacaaaacac agcaaaacac aaaaattcta gataaaatgt taaagttatt gtccttgatg   1200
```

| | |
|---|---|
| gtcccattag cttctgcagc tgttatccac agacgtgatg ctaacatttc agctattgca | 1260 |
| tccgaatgga actccacttc taactcttct tcatctttat ctttaaacag accagctgtc | 1320 |
| cattattctc cagaggaagg ttggatgaac gacccaaacg gtttatggta cgatgctaaa | 1380 |
| gaggaagatt ggcacatcta ctatcaatac tatcctgatg cccctcattg ggttttgcca | 1440 |
| ttgacttggg gtcatgcagt ctccaaagat ttgaccgtct gggacgaaca aggtgttgca | 1500 |
| ttcggtccag agtttgaaac agcaggtgcc ttttctggtt ctatggttat tgattacaat | 1560 |
| aacacctccg gtttctttaa ctcatccacc gacccaagac aacgtgtcgt tgccatttgg | 1620 |
| actttggatt attctggctc tgaaacacaa caattatctt attctcatga tggtggttat | 1680 |
| acattcaccg aatattctga caaccctgtc ttagatattg actcagacgc ttttagagat | 1740 |
| ccaaaggttt tctggtatca aggtgaagat tccgaatcag aaggtaactg ggtcatgaca | 1800 |
| gttgccgaag cagatcgttt ctccgtctta atctactctt ctccagacct taagaattgg | 1860 |
| acctagaat caaactttc cagagaaggc tacttaggct ataactatga gtgtcctggt | 1920 |
| ttagttaagg tcccatacgt caaaaacacc acatacgcat ctgctccagg ctcaaatatc | 1980 |
| acctcatctg gtccacttca tccaaattct actgtttctt tctcaaattc atcctctatt | 2040 |
| gcatggaatg cttcttccgt tccacttaac attactttat ccaattctac cttggttgat | 2100 |
| gaaacttctc aattggaaga agttggttac gcatgggtta tgattgtctc attcaatcct | 2160 |
| ggctccattt taggcggttc cggtactgaa tacttcatcg gtgactttaa tggtacacac | 2220 |
| ttcgagccac ttgataagca aactagattc ttagatttgg gtaaagatta ctacgctttg | 2280 |
| caaactttct tcaataccc aaacgaggtt gacgttttgg gtatcgcatg ggcctctaat | 2340 |
| tggcaatatg ctaaccaagt tccaacagat ccatggagat catccatgtc cttggttaga | 2400 |
| aacttcacta tcactgaata caacatcaat tctaatacta ctgcattggt cttgaactct | 2460 |
| caaccagttt tagattttac ctcttttaaga aagaacggca catcatatac tttagagaat | 2520 |
| cttacattaa actcctcttc tcacgaggtt ttggaatttg aagatcctac cggtgttttc | 2580 |
| gaattttccc ttgaatattc cgtcaacttt accggtattc acaactgggt ttttaccgac | 2640 |
| ttgtccttgt atttccaagg tgataaggat tcagatgaat acttgagact tggttacgaa | 2700 |
| gctaactcca agcagttctt tttagataga ggtcattcta acattccatt tgttcaagaa | 2760 |
| aatccattct tcactcagag actttcagtt tccaatcctc catcctccaa ctcctccacc | 2820 |
| ttcgatgtct acggtattgt tgacagaaat atcattgaat tgtatttcaa caatggtact | 2880 |
| gttacctcta ctaacaccct tttcttctcc actggtaaca atattggttc catcattgtt | 2940 |
| aagtctggtg ttgatgacgt ctatgaaatt gaatcattga aggttaatca gttttacgtt | 3000 |
| gactaattaa ttaacatctg aatgtaaaat gaacattaaa atgaattact aaactttacg | 3060 |
| tctactttac aatctataaa ctttgtttaa tcatataacg aaatacacta atacacaatc | 3120 |
| ctgtacgtat gtaatacttt tatccatcaa ggattgagaa aaaaagtaa tgattccctg | 3180 |
| ggccattaaa acttagaccc ccaagcttgg ataggtcact ctctattttc gtttctccct | 3240 |
| tccctgatag aagggtgata tgtaattaag aataatatat aattttataa taaaagaatt | 3300 |
| catagcctca tgaaatcagc catttgcttt tgttcaacga tcttttgaaa ttgttgttgt | 3360 |
| tcttggtagt taagttgatc catcttggct tatgttgtgt gtatgttgta gttattctta | 3420 |
| gtatattcct gtcctgagtt tagtgaaaca taatatcgcc ttgaaatgaa atgctgaaa | 3480 |
| ttcgtcgaca tacaattttt caaactttt tttttctg gtgcacggac atgttttaa | 3540 |

```
aggaagtact ctataccagt tattcttcac aaatttaatt gctggagaat agatcttcaa      3600
cgctttaata aagtagtttg tttgtcaagg atggcgtcat acaaagaaag atcagaatca      3660
cacacttccc ctgttgctag gagactttc tccatcatgg aggaaaagaa gtctaacctt       3720
tgtgcatcat tggatattac tgaaactgaa aagcttctct ctattttgga cactattggt      3780
ccttacatct gtctagttaa aacacacatc gatattgttt ctgattttac gtatgaagga      3840
actgtgttgc ctttgaagga gcttgccaag aaacataatt ttatgatttt tgaagataga      3900
aaatttgctg atattggtaa cactgttaaa aatcaatata atctggtgt cttccgtatt       3960 gccgaatggg ctgacatcac taatgcacat ggtgtaacgg gtgcaggtat tgtttctggc      4020
ttgaaggagg cagcccaaga aacaaccagt gaacctagag gtttgctaat gcttgctgag      4080
ttatcatcaa agggttcttt agcatatggt gaatatacag aaaaaacagt agaaattgct      4140
aaatctgata aagagtttgt cattggtttt attgcgcaac acgatatggg cggtagagaa      4200
gaaggttttg actggatcat tatgactcca ggggttggtt tagatgacaa aggtgatgca      4260
cttggtcaac aatatagaac tgttgatgaa gttgtaaaga ctggaacgga tatcataatt      4320
gttggtagag gtttgtacgg tcaaggaaga gatcctatag agcaagctaa aagataccaa      4380
caagctggtt ggaatgctta tttaaacaga tttaaatgat tcttacacaa agatttgata      4440
catgtacact agttaaaata agcatgaaaa gaattacaca agcaaaaaaa aaaaataaa      4500 tgaggtactt tacgttcacc tacaaccaaa aaaactagat agagtaaaat cttaagattt      4560 agaaaagtt gtttaacaaa ggctttagta tgtgaatttt taatgtagca aagcgataac       4620
taataaacat aaacaaaagt atggttttct ttatcagtca aatcattatc gattgattgt      4680
tccgcgtatc tgcagatagc ctcatgaaat cagccatttg cttttgttca acgatctttt      4740
gaaattgttg ttgttcttgg tagttaagtt gatccatctt ggcttatgtt gtgtgtatgt      4800
tgtagttatt cttagtatat tcctgtcctg agtttagtga aacataatat cgccttgaaa      4860
tgaaaatgct gaaattcgtc gacatacaat ttttcaaact ttttttttt cttggtgcac      4920 ggacatgttt ttaaaggaag tactctatac cagttattct tcacaaattt aattgctgga      4980
gaatagatct tcaacgcccc gggggatctg gatccgcggc cgcgagctct aatgattcaa      5040
gaaaaagttc aaataaacta atggatcaac ctatttcgac cctttcttca ttgctacttc      5100
ttccttaagc aacagatgat taagtagata ctgtttttt agccaatagt atctcgccga      5160
ggagttatac ttgactagct cttgctcaag aatcttccta agacgtacta gcctagcata      5220
gtaatctgtt tgtttctgta ttgtttgttc taactgttct acagtcattg aatcaatatc      5280
tccaatgtct tcgacgttga caactttccc ccccttggca gcattctctt ttttgttgga      5340
atacgacatt aaagattcct tgattttctg ggtaccttca atgaccattg agggattaaa      5400
tttgatttct ttgatttat aatggtcggc tattagctct tccacttcgt catcatgatc       5460
atcagatatg tcacgttgcc ttttcaattt attaaaattg tttatcagtt tattgtgatc      5520
ttgtatcaat tcattgcgta ctcttttctc aatatcaaaa gctatttct tcccgctaga       5580 ctcaaaatca actctgaagt catttctcg ctggaattca tgtatttcat ggattaattc       5640
tctattgata ttctcgtatg catcctgtaa actgttgccg ttgatattat gaaccgcctt      5700
taaatgtttc aataaggcat ctgctctagt aaatgccttc agacattcag gtaataaaca      5760
gtaaaatggc ttctcggctg tatgcgtcct aatgttt                               5797

<210> SEQ ID NO 6
<211> LENGTH: 609
```

```
<212> TYPE: PRT
<213> ORGANISM: Kluyveromyces lactis

<400> SEQUENCE: 6

Met Leu Lys Leu Leu Ser Leu Met Val Pro Leu Ala Ser Ala Ala Val
1               5                   10                  15

Ile His Arg Arg Asp Ala Asn Ile Ser Ala Ile Ala Ser Glu Trp Asn
                20                  25                  30

Ser Thr Ser Asn Ser Ser Ser Leu Ser Leu Asn Arg Pro Ala Val
                35                  40                  45

His Tyr Ser Pro Glu Glu Gly Trp Met Asn Asp Pro Asn Gly Leu Trp
            50                  55                  60

Tyr Asp Ala Lys Glu Glu Asp Trp His Ile Tyr Gln Tyr Tyr Pro
65                  70                  75                  80

Asp Ala Pro His Trp Gly Leu Pro Leu Thr Trp Gly His Ala Val Ser
                    85                  90                  95

Lys Asp Leu Thr Val Trp Asp Glu Gln Gly Val Ala Phe Gly Pro Glu
                100                 105                 110

Phe Glu Thr Ala Gly Ala Phe Ser Gly Ser Met Val Ile Asp Tyr Asn
            115                 120                 125

Asn Thr Ser Gly Phe Phe Asn Ser Ser Thr Asp Pro Arg Gln Arg Val
130                 135                 140

Val Ala Ile Trp Thr Leu Asp Tyr Ser Gly Ser Glu Thr Gln Gln Leu
145                 150                 155                 160

Ser Tyr Ser His Asp Gly Gly Tyr Thr Phe Thr Glu Tyr Ser Asp Asn
                165                 170                 175

Pro Val Leu Asp Ile Asp Ser Asp Ala Phe Arg Asp Pro Lys Val Phe
                180                 185                 190

Trp Tyr Gln Gly Glu Asp Ser Glu Ser Glu Gly Asn Trp Val Met Thr
                195                 200                 205

Val Ala Glu Ala Asp Arg Phe Ser Val Leu Ile Tyr Ser Ser Pro Asp
    210                 215                 220

Leu Lys Asn Trp Thr Leu Glu Ser Asn Phe Ser Arg Glu Gly Tyr Leu
225                 230                 235                 240

Gly Tyr Asn Tyr Glu Cys Pro Gly Leu Val Lys Val Pro Tyr Val Lys
                245                 250                 255

Asn Thr Thr Tyr Ala Ser Ala Pro Gly Ser Asn Ile Thr Ser Ser Gly
                260                 265                 270

Pro Leu His Pro Asn Ser Thr Val Ser Phe Ser Asn Ser Ser Ile
                275                 280                 285

Ala Trp Asn Ala Ser Ser Val Pro Leu Asn Ile Thr Leu Ser Asn Ser
                290                 295                 300

Thr Leu Val Asp Glu Thr Ser Gln Leu Glu Val Gly Tyr Ala Trp
305                 310                 315                 320

Val Met Ile Val Ser Phe Asn Pro Gly Ser Ile Leu Gly Gly Ser Gly
                325                 330                 335

Thr Glu Tyr Phe Ile Gly Asp Phe Asn Gly Thr His Phe Glu Pro Leu
                340                 345                 350

Asp Lys Gln Thr Arg Phe Leu Asp Leu Gly Lys Asp Tyr Tyr Ala Leu
                355                 360                 365

Gln Thr Phe Phe Asn Thr Pro Asn Glu Val Asp Val Leu Gly Ile Ala
            370                 375                 380

Trp Ala Ser Asn Trp Gln Tyr Ala Asn Gln Val Pro Thr Asp Pro Trp
385                 390                 395                 400
```

Arg Ser Ser Met Ser Leu Val Arg Asn Phe Thr Ile Thr Glu Tyr Asn
                405                 410                 415

Ile Asn Ser Asn Thr Thr Ala Leu Val Leu Asn Ser Gln Pro Val Leu
            420                 425                 430

Asp Phe Thr Ser Leu Arg Lys Asn Gly Thr Ser Tyr Thr Leu Glu Asn
        435                 440                 445

Leu Thr Leu Asn Ser Ser His Glu Val Leu Glu Phe Glu Asp Pro
    450                 455                 460

Thr Gly Val Phe Glu Phe Ser Leu Glu Tyr Ser Val Asn Phe Thr Gly
465                 470                 475                 480

Ile His Asn Trp Val Phe Thr Asp Leu Ser Leu Tyr Phe Gln Gly Asp
                485                 490                 495

Lys Asp Ser Asp Glu Tyr Leu Arg Leu Gly Tyr Glu Ala Asn Ser Lys
            500                 505                 510

Gln Phe Phe Leu Asp Arg Gly His Ser Asn Ile Pro Phe Val Gln Glu
        515                 520                 525

Asn Pro Phe Phe Thr Gln Arg Leu Ser Val Ser Asn Pro Pro Ser Ser
    530                 535                 540

Asn Ser Ser Thr Phe Asp Val Tyr Gly Ile Val Asp Arg Asn Ile Ile
545                 550                 555                 560

Glu Leu Tyr Phe Asn Asn Gly Thr Val Thr Ser Thr Asn Thr Phe Phe
                565                 570                 575

Phe Ser Thr Gly Asn Asn Ile Gly Ser Ile Ile Val Lys Ser Gly Val
            580                 585                 590

Asp Asp Val Tyr Glu Ile Glu Ser Leu Lys Val Asn Gln Phe Tyr Val
        595                 600                 605

Asp

<210> SEQ ID NO 7
<211> LENGTH: 703
<212> TYPE: DNA
<213> ORGANISM: Issatchenkia orientalis

<400> SEQUENCE: 7
gagtccatcg gttcctgtca gatgggatac tcttgacgtg gaaaattcaa acagaaaaaa      60
aaccccaata atgaaaaata acactacgtt atatccgtgg tatcctctat cgtatcgtat     120
cgtagcgtat cgtagcgtac cgtatcacag tatagtctaa tattccgtat cttattgtat     180
cctatcctat tcgatcctat tgtatttcag tgcaccattt taatttctat tgctataatg     240
tccttattag ttgccactgt gaggtgacca atggacgagg gcgagccgtt cagaagccgc     300
gaagggtgtt cttcccatga atttcttaag gagggcggct cagctccgag agtgaggcga     360
gacgtctcgg ttagcgtatc ccccttcctc ggcttttaca aatgatgcgc tcttaatagt     420
gtgtcgttat cctttggca ttgacggggg agggaaattg attgagcgca tccatatttt     480
ggcggactgc tgaggacaat ggtggttttt ccgggtggcg tgggctacaa atgatacgat     540 ggttttttc ttttcggaga aggcgtataa aaggacacg gagaacccat ttattctaat      600
aacagttgag cttctttaat tatttgttaa tataatattc tattattata tattttcttc     660
ccaataaaac aaaataaaac aaaacacagc aaaacacaaa aat                       703

<210> SEQ ID NO 8
<211> LENGTH: 5598
<212> TYPE: DNA
<213> ORGANISM: Artificial Sequence
<220> FEATURE:
<223> OTHER INFORMATION: URA3-invertase-locus A transformation sequence

<400> SEQUENCE: 8

| | | | | | |
|---|---|---|---|---|---|
| aaaccataat | gcgtgacacc | gccatgatgg | ttgtattcta | ccaatgagac | atggccgctg | 60 |
| atcctgttgt | gtgggtcatg | ggacatcacc | tcttgggggg | gattctccta | taattggcac | 120 |
| cgtgtatgcc | tcaaccacta | acttccaccc | tataactgaa | tatattacat | aagcaaatct | 180 |
| acttttttgtt | tgtgttgatc | gccatcgttg | aaattcgcgc | aacttctggt | ggctcaacgc | 240 |
| tgctgttcta | tcggtatcct | aagagatgtc | tttgccctga | gtctagggta | aactatccac | 300 |
| cttcgttgct | gtttgactag | acagctacta | actttacggt | agtaaatgaa | taacggctcg | 360 |
| ctctcatgat | cacttctcta | catcacccta | acaagtgtat | tattttttt | tcaggtgggt | 420 |
| gttgctgttg | gtgctagcat | atggcggccg | cggatccctc | gaggtggtca | atgtttaact | 480 |
| agaattatag | gccaatctta | tcttctccga | attcattgca | gccaccatca | atttaacatt | 540 |
| ggttttcaaa | taatcagtta | aacctgacag | tgattaccag | ccacggggat | tcgagaaatt | 600 |
| cgagcaattc | gaaagagccg | caaaaaaata | agcaagaaaa | agaaaataa | aaacaaaaa | 660 |
| aaacatgaaa | aaaacatgaa | aaaaacatga | aaaaaaaaaa | aagaaagaa | aaaaaaaatc | 720 |
| aatttttttca | tcagaggcat | tggtaaaaca | ctctgtgctg | tcgcgacacg | acgaacggga | 780 |
| tgccatggta | cttgtttcgg | gtgtctctcc | tcctttggaa | actctttccg | ctctcgaaaa | 840 |
| aattaatacc | gtagaggagg | ggacatgaat | agaatcgtat | ataacagggt | cattccctga | 900 |
| tgctgtctttt | gtaaggagcc | atttattgtc | atttgtttat | accaacccca | ttgaacaaac | 960 |
| aagaaaatct | agataaaatg | ttaaagttat | tgtccttgat | ggtcccatta | gcttctgcag | 1020 |
| ctgttatcca | cagacgtgat | gctaacattt | cagctattgc | atccgaatgg | aactccactt | 1080 |
| ctaactcttc | ttcatctttta | tctttaaaca | gaccagctgt | ccattattct | ccagaggaag | 1140 |
| gttggatgaa | cgacccaaac | ggtttatggt | acgatgctaa | agaggaagat | tggcacatct | 1200 |
| actatcaata | ctatcctgat | gcccctcatt | ggggtttgcc | attgacttgg | ggtcatgcag | 1260 |
| tctccaaaga | tttgaccgtc | tgggacgaac | aaggtgttgc | attcggtcca | gagtttgaaa | 1320 |
| cagcaggtgc | cttttctggt | tctatggtta | ttgattacaa | taacacctcc | ggtttctttta | 1380 |
| actcatccac | cgacccaaga | caacgtgtcg | ttgccatttg | gactttggat | tattctggct | 1440 |
| ctgaaacaca | acaattatct | tattctcatg | atggtggtta | tacattcacc | gaatattctg | 1500 |
| acaaccctgt | cttagatatt | gactcagacg | cttttagaga | tccaaaggtt | ttctggtatc | 1560 |
| aaggtgaaga | ttccgaatca | gaaggtaact | gggtcatgac | agttgccgaa | gcagatcgtt | 1620 |
| tctccgtctt | aatctactct | tctccagacc | ttaagaattg | gaccttagaa | tcaaactttt | 1680 |
| ccagagaagg | ctacttaggc | tataactatg | agtgtcctgg | tttagttaag | gtcccatacg | 1740 |
| tcaaaaacac | cacatacgca | tctgctccag | gctcaaatat | cacctcatct | ggtccacttc | 1800 |
| atccaaattc | tactgtttct | ttctcaaatt | catcctctat | tgcatggaat | gcttcttccg | 1860 |
| ttccacttaa | cattactttta | tccaattcta | ccttggttga | tgaaacttct | caattggaag | 1920 |
| aagttggtta | cgcatgggtt | atgattgtct | cattcaatcc | tggctccatt | ttaggcggtt | 1980 |
| ccggtactga | atacttcatc | ggtgactttta | atggtacaca | cttcgagcca | cttgataagc | 2040 |
| aaactagatt | cttagatttg | ggtaaagatt | actacgcttt | gcaaactttc | ttcaataccc | 2100 |
| caaacgaggt | tgacgttttg | ggtatcgcat | gggcctctaa | ttggcaatat | gctaaccaag | 2160 |
| ttccaacaga | tccatggaga | tcatccatgt | ccttggttag | aaacttcact | atcactgaat | 2220 |

```
acaacatcaa ttctaatact actgcattgg tcttgaactc tcaaccagtt ttagatttta    2280
cctctttaag aaagaacggc acatcatata ctttagagaa tcttacatta aactcctctt    2340
ctcacgaggt tttggaattt gaagatccta ccggtgtttt cgaattttcc cttgaatatt    2400
ccgtcaactt taccggtatt cacaactggg ttttaccga cttgtccttg tatttccaag     2460
gtgataagga ttcagatgaa tacttgagac ttggttacga agctaactcc aagcagttct    2520
ttttagatag aggtcattct aacattccat ttgttcaaga aaatccattc ttcactcaga    2580
gactttcagt ttccaatcct ccatcctcca actcctccac cttcgatgtc tacggtattg    2640
ttgacagaaa tatcattgaa ttgtatttca acaatggtac tgttacctct actaacacct    2700
ttttcttctc cactggtaac aatattggtt ccatcattgt taagtctggt gttgatgacg    2760
tctatgaaat tgaatcattg aaggttaatc agttttacgt tgactaatta attaacatct    2820
gaatgtaaaa tgaacattaa aatgaattac taaactttac gtctacttta caatctataa    2880
actttgttta atcatataac gaaatacact aatacacaat cctgtacgta tgtaatactt    2940
ttatccatca aggattgaga aaaaaagta atgattccct gggccattaa aacttagacc      3000
cccaagcttg gataggtcac tctctatttt cgtttctccc ttccctgata gaagggtgat    3060
atgtaattaa gaataatata taatttata ataaagaat tcatagcctc atgaaatcag       3120
ccatttgctt ttgttcaacg atcttttgaa attgttgttg ttcttggtag ttaagttgat    3180
ccatcttggc ttatgttgtg tgtatgttgt agttattctt agtatattcc tgtcctgagt    3240
ttagtgaaac ataatatcgc cttgaaatga aaatgctgaa attcgtcgac atacaatttt    3300
tcaaactttt ttttttcttt ggtgcacgga catgttttta aaggaagtac tctataccag    3360
ttattcttca caaatttaat tgctggagaa tagatcttca acgctttaat aaagtagttt    3420
gtttgtcaag gatggcgtca tacaaagaaa gatcagaatc acacacttcc cctgttgcta    3480
ggagactttt ctccatcatg gaggaaaaga agtctaacct tgtgcatca ttggatatta     3540 ctgaaactga aaagcttctc tctatttgg acactattgg tccttacatc tgtctagtta     3600
aaacacacat cgatattgtt tctgatttta cgtatgaagg aactgtgttg cctttgaagg    3660
agcttgccaa gaaacataat tttatgattt ttgaagatag aaaatttgct gatattggta    3720
acactgttaa aaatcaatat aaatctggtg tcttccgtat tgccgaatgg gctgacatca    3780
ctaatgcaca tggtgtaacg ggtgcaggta ttgtttctgg cttgaaggag gcagcccaag    3840
aaacaaccag tgaacctaga ggtttgctaa tgcttgctga gttatcatca aagggttctt    3900
tagcatatgg tgaatataca gaaaaaacag tagaaattgc taaatctgat aaagagtttg    3960
tcattggttt tattgcgcaa cacgatatgg gcggtagaga agaaggtttt gactggatca    4020
ttatgactcc aggggttggt ttagatgaca aaggtgatgc acttggtcaa caatatagaa    4080
ctgttgatga agttgtaaag actggaacgg atatcataat tgttggtaga ggtttgtacg    4140
gtcaaggaag agatcctata gagcaagcta aagatacca acaagctggt tggaatgctt     4200
atttaaacag atttaaatga ttcttacaca agatttgat acatgtacac tagttttaaat    4260 aagcatgaaa agaattacac aagcaaaaaa aaaaaataa atgaggtact ttacgttcac    4320
ctacaaccaa aaaactaga tagagtaaaa tcttaagatt tagaaaaagt tgtttaacaa    4380
aggctttagt atgtgaattt ttaatgtagc aaagcgataa ctaataaaca taaacaaaag    4440
tatggttttc tttatcagtc aaatcattat cgattgattg ttccgcgtat ctgcagatag    4500
cctcatgaaa tcagccattt gcttttgttc aacgatcttt tgaaattgtt gttgttcttg    4560
gtagttaagt tgatccatct tggcttatgt tgtgtgtatg ttgtagttat tcttagtata    4620
```

```
ttcctgtcct gagtttagtg aaacataata tcgccttgaa atgaaaatgc tgaaattcgt    4680
cgacatacaa ttttttcaaac ttttttttt tcttggtgca cggacatgtt tttaaaggaa    4740
gtactctata ccagttattc ttcacaaatt taattgctgg agaatagatc ttcaacgccc    4800
cgggggatct ggatccgcgg ccgcgagctc taatgattca agaaaagtt caaataaact     4860 aatggatcaa cctatttcga ccctttcttc attgctactt cttccttaag caacagatga    4920
ttaagtagat actgttttt tagccaatag tatctcgccg aggagttata cttgactagc     4980
tcttgctcaa gaatcttcct aagacgtact agcctagcat agtaatctgt tgtttctgt     5040 attgtttgtt ctaactgttc tacagtcatt gaatcaatat ctccaatgtc ttcgacgttg    5100
acaactttcc cccccttggc agcattctct tttttgttgg aatacgacat taaagattcc    5160
ttgattttct gggtaccttc aatgaccatt gagggattaa atttgatttc tttgatttta    5220
taatggtcgg ctattagctc ttccacttcg tcatcatgat catcagatat gtcacgttgc    5280
cttttcaatt tattaaaatt gtttatcagt ttattgtgat cttgtatcaa ttcattgcgt    5340
actcttttct caatatcaaa agctattttc ttcccgctag actcaaaatc aactctgaag    5400
tcattttctc gctggaattc atgtatttca tggattaatt ctctattgat attctcgtat    5460
gcatcctgta aactgttgcc gttgatatta tgaaccgcct ttaaatgttt caataaggca    5520
tctgctctag taaatgcctt cagacattca ggtaataaac agtaaaatgg cttctcggct    5580
gtatgcgtcc taatgttt                                                  5598

<210> SEQ ID NO 9
<211> LENGTH: 453
<212> TYPE: DNA
<213> ORGANISM: Issatchenkia orientalis

<400> SEQUENCE: 9
attgcagcca ccatcaattt aacattggtt ttcaaataat cagttaaacc tgacagtgat      60
taccagccac ggggattcga gaaattcgag caattcgaaa gagccgcaaa aaaataagca     120
agaaaaaaga aaataaaaaa caaaaaaaac atgaaaaaaa catgaaaaaa acatgaaaaa     180 aaaaaaaag aaagaaaaaa aaaatcaatt ttttcatcag aggcattggt aaaacactct     240
gtgctgtcgc gacacgacga acgggatgcc atggtacttg tttcgggtgt ctctcctcct     300
ttggaaactc tttccgctct cgaaaaaatt aataccgtag aggagggac atgaatagaa      360 tcgtatataa cagggtcatt ccctgatgct gtctttgtaa ggagccattt attgtcatttt    420 gtttatacca accccattga acaaacaaga aaa                                 453

<210> SEQ ID NO 10
<211> LENGTH: 6015
<212> TYPE: DNA
<213> ORGANISM: Artificial Sequence
<220> FEATURE:
<223> OTHER INFORMATION: URA3-invertase-locus A transformation sequence

<400> SEQUENCE: 10
aaaccataat gcgtgacacc gccatgatgg ttgtattcta ccaatgagac atggccgctg      60
atcctgttgt gtgggtcatg ggacatcacc tcttgggggg gattctccta taattggcac    120
cgtgtatgcc tcaaccacta acttccaccc tataactgaa tatattacat aagcaaatct    180 acttttgtt tgtgttgatc gccatcgttg aaattcgcgc aacttctggt ggctcaacgc    240
tgctgttcta tcggtatcct aagagatgtc tttgccctga gtctagggta aactatccac    300
```

```
cttcgttgct gtttgactag acagctacta actttacggt agtaaatgaa taacggctcg    360
ctctcatgat cacttctcta catcaccta acaagtgtat tatttttttt tcaggtgggt    420
gttgctgttg gtgctagcat atggcggccg cggatccctc gagtttggat gaggcattca    480
atgtctccat gtttgaagac cagagaaagt gtaggtaaca caatagccat ggacaattag    540
cgaatccgaa tatgtgtact aacattgtgc ctccaactga cagctggtcg aataatgatt    600
gaaatcatca acatatcag agatatatcc cagaaccatt taacaactgt tattgtatgt    660
atgcattact gttttacatt gtgtctttcc aaatactaac attgccatta tccaatccat    720
acatatatat atatatagat tacacaacgc aaacctcgac agtcgattgg tttacatcgt    780
gtaagcagcc ttttacggaa tatgatggac aaccagatcc tcatagatgg agacaatgtg    840
cagatagatt ccatttatga tgacattgat gtgttttttaa atgcaaaata atctcctata    900
taagtgagtt ccgagtctcc ccatgcttat cttatcgtgt ttttctgta aattaggtca    960 aagtattcaa acaattccct caatctttcc cattttttgc tgagccccca tatcatcaaa   1020
ttaacgtatc aaatttccta attagtagcc ccgtatgtta aattagacat gtgtgactgc   1080
catcccggac agcctaccca atgacacccg cgcaccgcac atattgtgtt tagtgcgcgc   1140
cgtctgctga agcgactccc tgtttgggag gaaccgaggg cgggttgccc gatcccttgc   1200
ccctcgctcc tcctcctggg ctcccccttg cagagggaca ccgaggggat ccctcgtgtg   1260
agagcttgga ggtggatggt ggtcaatttt ctcatttgat tgaaagattt gttatattga   1320
aaattcagtt tgtggaagtt gtgattaaaa ggttttactg tttgttctgt agacacattc   1380
aatatctaga taaaatgtta aagttattgt ccttgatggt cccattagct tctgcagctg   1440
ttatccacag acgtgatgct aacatttcag ctattgcatc cgaatggaac tccacttcta   1500
actcttcttc atctttatct ttaaacagac cagctgtcca ttattctcca gaggaaggtt   1560
ggatgaacga cccaaacggt ttatggtacg atgctaaaga ggaagattgg cacatctact   1620
atcaatacta tcctgatgcc cctcattggg gtttgccatt gacttggggt catgcagtct   1680
ccaaagattt gaccgtctgg gacgaacaag gtgttgcatt cggtccagag tttgaaacag   1740
caggtgcctt ttctggttct atggttattg attacaataa cacctccggt ttctttaact   1800
catccaccga cccaagacaa cgtgtcgttg ccatttggac tttggattat tctggctctg   1860
aaacacaaca attatcttat tctcatgatg gtggttatac attcaccgaa tattctgaca   1920
accctgtctt agatattgac tcagacgctt ttagagatcc aaaggttttc tggtatcaag   1980
gtgaagattc cgaatcagaa ggtaactggg tcatgacagt tgccgaagca gatcgtttct   2040
ccgtcttaat ctactcttct ccagaccttta agaattggac cttagaatca aacttttcca   2100
gagaaggcta cttaggctat aactatgagt gtcctggttt agttaaggtc ccatacgtca   2160
aaaacaccac atacgcatct gctccaggct caaatatcac ctcatctggt ccacttcatc   2220
caaattctac tgtttctttc tcaaattcat cctctattgc atggaatgct tcttccgttc   2280
cacttaacat tactttatcc aattctacct tggttgatga aacttctcaa ttggaagaag   2340
ttggttacgc atgggttatg attgtctcat tcaatcctgg ctccatttta ggcggttccg   2400
gtactgaata cttcatcggt gactttaatg gtacacactt cgagccactt gataagcaaa   2460
ctagattctt agatttgggt aaagattact acgctttgca aactttcttc aatacccaa   2520 acgaggttga cgttttgggt atcgcatggg cctctaattg gcaatatgct aaccaagttc   2580
caacagatcc atggagatca tccatgtcct tggttagaaa cttcactatc actgaataca   2640
acatcaattc taatactact gcattggtct tgaactctca accagtttta gattttacct   2700
```

```
ctttaagaaa gaacggcaca tcatatactt tagagaatct tacattaaac tcctcttctc    2760
acgaggtttt ggaatttgaa gatcctaccg gtgttttcga attttcccct gaatattccg    2820
tcaactttac cggtattcac aactgggttt ttaccgactt gtccttgtat ttccaaggtg    2880
ataaggattc agatgaatac ttgagacttg gttacgaagc taactccaag cagttctttt    2940
tagatagagg tcattctaac attccatttg ttcaagaaaa tccattcttc actcagagac    3000
tttcagtttc caatcctcca tcctccaact cctccacctt cgatgtctac ggtattgttg    3060
acagaaatat cattgaattg tatttcaaca atggtactgt tacctctact aacacctttt    3120
tcttctccac tggtaacaat attggttcca tcattgttaa gtctggtgtt gatgacgtct    3180
atgaaattga atcattgaag gttaatcagt tttacgttga ctaattaatt aacatctgaa    3240
tgtaaaatga acattaaaat gaattactaa actttacgtc tactttacaa tctataaact    3300
ttgtttaatc atataacgaa atacactaat acacaatcct gtacgtatgt aatactttta    3360
tccatcaagg attgagaaaa aaagtaatg attccctggg ccattaaaac ttagaccccc    3420
aagcttggat aggtcactct ctattttcgt ttctcccttc cctgatagaa gggtgatatg    3480
taattaagaa taatatataa ttttataata aaagaattca tagcctcatg aaatcagcca    3540
tttgcttttg ttcaacgatc ttttgaaatt gttgttgttc ttggtagtta agttgatcca    3600
tcttggctta tgttgtgtgt atgttgtagt tattcttagt atattcctgt cctgagttta    3660
gtgaaacata atatcgcctt gaaatgaaaa tgctgaaatt cgtcgacata caattttca    3720 aactttttt ttttcttggt gcacggacat gttttttaaag gaagtactct ataccagtta    3780
ttcttcacaa atttaattgc tggagaatag atcttcaacg ctttaataaa gtagtttgtt    3840
tgtcaaggat ggcgtcatac aaagaaagat cagaatcaca cacttcccct gttgctagga    3900
gacttttctc catcatggag gaaaagaagt ctaacctttg tgcatcattg gatattactg    3960
aaactgaaaa gcttctctct attttggaca ctattggtcc ttacatctgt ctagttaaaa    4020
cacacatcga tattgtttct gattttacgt atgaaggaac tgtgttgcct ttgaaggagc    4080
ttgccaagaa acataatttt atgatttttg aagatagaaa atttgctgat attggtaaca    4140
ctgttaaaaa tcaatataaa tctggtgtct tccgtattgc cgaatgggct gacatcacta    4200
atgcacatgg tgtaacgggt gcaggtattg tttctggctt gaaggaggca gcccaagaaa    4260
caaccagtga acctagaggt ttgctaatgc ttgctgagtt atcatcaaag ggttctttag    4320
catatggtga atatacagaa aaaacagtag aaattgctaa atctgataaa gagtttgtca    4380
ttggttttat tgcgcaacac gatatgggcg gtagagaaga aggttttgac tggatcatta    4440
tgactccagg ggttggttta gatgacaaag gtgatgcact tggtcaacaa tatagaactg    4500
ttgatgaagt tgtaaagact ggaacggata tcataattgt tggtagaggt ttgtacggtc    4560
aaggaagaga tcctatagag caagctaaaa gataccaaca agctggttgg aatgcttatt    4620
taaacagatt taaatgattc ttacacaaag atttgataca tgtacactag tttaaataag    4680
catgaaaaga attacacaag caaaaaaaaa aaaataaatg aggtacttta cgttcaccta    4740
caaccaaaaa aactagatag agtaaaatct taagatttag aaaaagttgt ttaacaaagg    4800
ctttagtatg tgaattttta atgtagcaaa gcgataacta ataaacataa acaaaagtat    4860
ggttttcttt atcagtcaaa tcattatcga ttgattgttc cgcgtatctg cagatagcct    4920
catgaaatca gccatttgct tttgttcaac gatctttga aattgttgtt gttcttggta    4980
gttaagttga tccatcttgg cttatgttgt gtgtatgttg tagttattct tagtatattc    5040
```

```
ctgtcctgag tttagtgaaa cataatatcg ccttgaaatg aaaatgctga aattcgtcga      5100
catacaattt ttcaaacttt ttttttttct tggtgcacgg acatgttttt aaaggaagta      5160
ctctatacca gttattcttc acaaatttaa ttgctggaga atagatcttc aacgccccgg      5220
gggatctgga tccgcggccg cgagctctaa tgattcaaga aaaagttcaa ataaactaat      5280
ggatcaacct atttcgaccc tttcttcatt gctacttctt ccttaagcaa cagatgatta      5340
agtagatact gttttttttag ccaatagtat ctcgccgagg agttatactt gactagctct      5400
tgctcaagaa tcttcctaag acgtactagc ctagcatagt aatctgtttg tttctgtatt      5460
gtttgttcta actgttctac agtcattgaa tcaatatctc caatgtcttc gacgttgaca      5520
actttccccc ccttggcagc attctctttt ttgttggaat acgacattaa agattccttg      5580
attttctggg taccttcaat gaccattgag ggattaaatt tgatttcttt gattttataa      5640
tggtcggcta ttagctcttc cacttcgtca tcatgatcat cagatatgtc acgttgcctt      5700
ttcaatttat taaaattgtt tatcagttta ttgtgatctt gtatcaattc attgcgtact      5760
cttttctcaa tatcaaaagc tatttttcttc ccgctagact caaaatcaac ctgaagtca      5820 ttttctcgct ggaattcatg tatttcatgg attaattctc tattgatatt ctcgtatgca      5880
tcctgtaaac tgttgccgtt gatattatga accgccttta aatgtttcaa taaggcatct      5940
gctctagtaa atgccttcag acattcaggt aataaacagt aaaatggctt ctcggctgta      6000
tgcgtcctaa tgttt                                                      6015

<210> SEQ ID NO 11
<211> LENGTH: 921
<212> TYPE: DNA
<213> ORGANISM: Issatchenkia orientalis

<400> SEQUENCE: 11
tttggatgag gcattcaatg tctccatgtt tgaagaccag agaaagtgta ggtaacacaa        60
tagccatgga caattagcga atccgaatat gtgtactaac attgtgcctc caactgacag      120
ctggtcgaat aatgattgaa atcatcaaac atatcagaga tatatcccag aaccatttaa      180
caactgttat tgtatgtatg cattactgtt ttacattgtg tctttccaaa tactaacatt      240
gccattatcc aatccataca tatatatata tatagattac acaacgcaaa cctcgacagt      300
cgattggttt acatcgtgta agcagccttt tacggaatat gatggacaac cagatcctca      360
tagatggaga caatgtgcag atagattcca tttatgatga cattgatgtg ttttttaaatg      420 caaaataatc tcctatataa gtgagttccg agtctcccca tgcttatctt atcgtgtttt      480
ttctgtaaat taggtcaaag tattcaaaca attccctcaa tctttcccat ttttttgctga    540 gccccccatat catcaaatta acgtatcaaa tttcctaatt agtagccccg tatgttaaat     600
tagacatgtg tgactgccat cccggacagc ctacccaatg acacccgcgc accgcacata      660
ttgtgtttag tgcgcgccgt ctgctgaagc gactccctgt ttgggaggaa ccgagggcgg      720
gttgcccgat cccttgcccc tcgctcctcc tcctgggctc cccccttgcag agggacaccg     780 agggggatccc tcgtgtgaga gcttggaggt ggatggtggt caattttctc atttgattga     840
aagatttgtt atattgaaaa ttcagtttgt ggaagttgtg attaaaaggt tttactgttt      900
gttctgtaga cacattcaat a                                                921

<210> SEQ ID NO 12
<211> LENGTH: 9630
<212> TYPE: DNA
<213> ORGANISM: Artificial Sequence
```

```
<220> FEATURE:
<223> OTHER INFORMATION: invertase-CRE recombinase transformation
      plasmid
<220> FEATURE:
<221> NAME/KEY: misc_feature
<222> LOCATION: (3086)..(3086)
<223> OTHER INFORMATION: n is a, c, g, or t
<220> FEATURE:
<221> NAME/KEY: misc_feature
<222> LOCATION: (5897)..(5897)
<223> OTHER INFORMATION: n is a, c, g, or t
<220> FEATURE:
<221> NAME/KEY: misc_feature
<222> LOCATION: (6283)..(6283)
<223> OTHER INFORMATION: n is a, c, g, or t
<220> FEATURE:
<221> NAME/KEY: misc_feature
<222> LOCATION: (6314)..(6314)
<223> OTHER INFORMATION: n is a, c, g, or t
<220> FEATURE:
<221> NAME/KEY: misc_feature
<222> LOCATION: (6343)..(6343)
<223> OTHER INFORMATION: n is a, c, g, or t
<220> FEATURE:
<221> NAME/KEY: misc_feature
<222> LOCATION: (6347)..(6347)
<223> OTHER INFORMATION: n is a, c, g, or t
<220> FEATURE:
<221> NAME/KEY: misc_feature
<222> LOCATION: (6371)..(6371)
<223> OTHER INFORMATION: n is a, c, g, or t
<220> FEATURE:
<221> NAME/KEY: misc_feature
<222> LOCATION: (6525)..(6525)
<223> OTHER INFORMATION: n is a, c, g, or t
<220> FEATURE:
<221> NAME/KEY: misc_feature
<222> LOCATION: (6543)..(6543)
<223> OTHER INFORMATION: n is a, c, g, or t
<220> FEATURE:
<221> NAME/KEY: misc_feature
<222> LOCATION: (7386)..(7386)
<223> OTHER INFORMATION: n is a, c, g, or t
<220> FEATURE:
<221> NAME/KEY: misc_feature
<222> LOCATION: (7397)..(7397)
<223> OTHER INFORMATION: n is a, c, g, or t

<400> SEQUENCE: 12
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg gctcccttta gggttccgat     180
ttagtgcttt acggcacctc gaccccaaaa aacttgatta gggtgatggt tcacgtagtg     240
ggccatcgcc ctgatagacg gttttttcgcc ctttgacgtt ggagtccacg ttctttaata    300
gtggactctt gttccaaact ggaacaacac tcaaccctat ctcggtctat tcttttgatt     360
tataagggat tttgccgatt tcggcctatt ggttaaaaaa tgagctgatt taacaaaaat    420
ttaacgcgaa ttttaacaaa atattaacgc ttacaatttc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggtcgagga    660
gtccatcggt tcctgtcaga tgggatactc ttgacgtgga aaattcaaac agaaaaaaaa    720
ccccaataat gaaaataac actacgttat atccgtggta tcctctatcg tatcgtatcg    780
tagcgtatcg tagcgtaccg tatcacagta tagtctaata ttccgtatct tattgtatcc    840
tatcctattc gatcctattg tatttcagtg caccatttta atttctattg ctataatgtc    900
```

```
cttattagtt gccactgtga ggtgaccaat ggacgagggc gagccgttca gaagccgcga     960
agggtgttct tcccatgaat ttcttaagga gggcggctca gctccgagag tgaggcgaga    1020
cgtctcggtc agcgtatccc ccttcctcgg cttttacaaa tgatgcgctc ttaatagtgt    1080
gtcgttatcc ttttggcatt gacggggag ggaaattgat tgagcgcatc catatttttg     1140
cggactgctg aggacaatgg tggttttcc gggtggcgtg ggctacaaat gatacgatgg     1200
ttttttcttt ttcggagaag gcgtataaaa aggacacgga gaacccattt attctaaaaa    1260
cagttgagct tctttaatta tttttgata taatattcta ttattatata ttttcttccc     1320
aataaaacaa aataaaacaa aacacagcaa aacacaaaaa ggatccatgt ctaatttact    1380
tactgttcac caaaacttgc ctgcattacc agttgacgca acctccgatg aagtcagaaa    1440
gaaccttatg gatatgttta gagatagaca agctttctcc gaacatactt ggaaaatgtt    1500
attatccgtt tgtagatcct gggccgcttg gtgtaaactt aacaatagaa aatggtttcc    1560
tgctgaacca gaagacgtca gagattactt actttactta caagctagag gtttggctgt    1620
taaaactatc caacaacact taggtcaatt gaatatgtta cacagaagat ccggtttacc    1680
aagaccatcc gattccaacg cagtttccct tgttatgaga agaattagaa aagaaaatgt    1740
tgacgctggt gaaagagcta acaagcatt agcatttgaa agaaccgatt tcgatcaagt     1800
tagatcctta atggaaaatt ccgatagatg tcaagatatt agaaacttag ctttcttagg    1860
tattgcttac aacacattat taagaatcgc tgaaattgct agaattagag ttaaagatat    1920
ttcaagaacc gatggcggta aatgttaat ccacattggc agaacaaaaa ccttagtctc     1980
cacagcaggc gtcgaaaaag cattatcatt aggtgttact aaattagttg aacgttggat    2040
ttccgtttcc ggtgttgcag atgacccaaa caactactta ttctgtcgtg ttagaaaaaa    2100
tggtgttgcc gctccttccg ctacctcaca attatccaca agagcattag aaggcatttt    2160
tgaagctacc cacagactta tttatggtgc aaaagacgat tccggtcaaa gatatttagc    2220
ttggtctggt cattccgcta gagttggtgc cgcaagagac atggcaagag ctggtgtttc    2280
tattcctgaa attatgcaag ccggtggttg gactaatgtt aacattgtta tgaactatat    2340
cagaaactta gattccgaaa caggtgctat ggttagatta cttgaagacg tgattaagt    2400 taattaacat ctgaatgtaa aatgaacatt aaaatgaatt actaaacttt acgtctactt    2460
tacaatctat aaactttgtt taatcatata acgaaataca ctaatacaca atcctgtacg    2520
tatgtaatac ttttatccat caaggattga gaaaaaaaag taatgattcc ctgggccatt    2580
aaaacttaga cccccaagct tggataggtc actctctatt ttcgtttctc ccttccctga    2640
tagaagggtg atatgtaatt aagaataata tataatttta taataaaaga attcggcaga    2700
tctggatcga tccccggc tgcatgcaac ggcaacatca atgtccacgt ttacacacct      2760
acatttatat ctatatttat atttatattt atttatttat gctacttagc ttctatagtt    2820
agttaatgca ctcacgatat tcaaaattga caccttcaa ctactcccta ctattgtcta     2880
ctactgtcta ctactcctct ttactatagc tgctcccaat aggctccacc aataggctct    2940
gtcaatacat tttgcgccgc cacctttcag gttgtgtcac tcctgaagga ccatattggg    3000
taatcgtgca atttctggaa gagagtgccg cgagaagtga ggcccccact gtaaatcctc    3060
gagggggcat ggagtatggg gcatgnagga tggaggatgg gggggggggg ggaaaatagg    3120
tagcgaaagg acccgctatc accccacccg gagaactcgt tgccgggaag tcatatttcg    3180
acactccggg gagtctataa aaggcgggtt ttgtcttttg ccagttgatg ttgctgagag    3240
```

```
gacttgtttg ccgtttcttc cgatttaaca gtatagaatc aaccactgtt aattatacac    3300
gttatactaa cacaacaaaa acaaaaacaa cgacaacaac aacaacctgc aggaaatgct    3360
tttgcaagct ttccttttcc ttttggctgg ttttgcagcc aaaatatctg catcaatgac    3420
aaacgaaact agcgatagac ctttggtcca cttcacaccc aacaagggct ggatgaatga    3480
cccaaatggg ttgtggtacg atgaaaaaga tgccaaatgg catctgtact ttcaatacaa    3540
cccaaatgac accgtatggg gtacgccatt gttttggggc catgctactt ccgatgattt    3600
gactcattgg gaagatgaac ccattgctat cgctcccaag cgtaacgatt caggtgcttt    3660
ctctggctcc atggtggttg attacaacaa cactagtggg tttttcaatg atactattga    3720
tccaagacaa agatgcgttg caatttggac ttataacact cctgaaagtg aagagcaata    3780
cattagctat tcccttgatg gtggttacac ttttactgaa taccaaaaga accctgtttt    3840
agctgccaac tccactcaat tcagagatcc aaaggtgttc tggtatgaac cttctcaaaa    3900
atggattatg acggctgcca atcacaaga ctacaaaatt gaaatttact cctcggatga    3960
cttgaagtcc tggaagttag aatctgcatt tgccaatgaa ggtttcttag ctaccaata    4020
tgaatgtcca ggtttgattg aagtcccaac tgagcaagat ccttccaaat cctattgggt    4080
catgtttatt tctatcaacc caggtgcacc tgctggcggt tccttcaacc aatattttgt    4140
tggatccttc aatggtactc attttgaagc gtttgacaat caatctagag tggtagattt    4200
tggtaaggac tactatgcct tgcaaacttt cttcaacact gacccaacct acggttcagc    4260
attaggtatt gcctgggctt caaactggga gtacagtgcc tttgtcccaa ctaacccatg    4320
gagatcatcc atgtctttgg tccgcaagtt ttcgttgaac actgaatatc aagctaatcc    4380
agagactgaa ttgatcaatt tgaaagccga accaatattg aacattagta atgctggccc    4440
ctggtctcgt tttgctacta acacaactct aactaaggcc aattcttaca atgtcgattt    4500
gagcaactcg actggtaccc tagagtttga gttggtttac gctgttaaca ccacacaaac    4560
catatccaaa tccgtctttg ccgacttatc actttggttc aagggtttag aagatcctga    4620
agaatatttg agaatgggtt ttgaagccag tgcttcttcc ttcttttttgg accgtggtaa    4680
ctctaaggtc aagtttgtca aggagaaccc atatttcaca aacagaatgt ctgtcaacaa    4740
ccaaccattc aagtctgaga cgacctaag ttactataaa gtgtacggcc tactggatca    4800
aaacatcttg gaattgtact tcaacgatgg agatgtggtt tctacaaata cctacttcat    4860
gaccaccggc aacgctctag gatctgtgaa catgaccact ggtgtcgata atttgttcta    4920
cattgacaag ttccaagtaa gggaagtaaa atagcctgca ggcacgtccg acggcggccc    4980
acgggtccca ggcctcggag atccgtcccc cttttccttt gtcgatatca tgtaattagt    5040
tatgtcacgc ttacattcac gccctccccc cacatccgct ctaaccgaaa aggaaggagt    5100
tagacaacct gaagtctagg tccctattta tttttttata gttatgttag tattaagaac    5160
gttatttata tttcaaattt ttcttttttt tctgtacaga cgcgtgtacg catgtaacat    5220
tatactgaaa accttgcttg agaaggtttt gggacgctcg aaggctttaa tttgcaagct    5280
gaattcccgg gccttaccgt cgacgaattt cagcattttc atttcaaggc gatattatgt    5340
ttcactaaac tcaggacagg aatatactaa gaataactac aacatacaca aacataagc    5400
caagatggat caacttaact accaagaaca acaacaattt caaaagatcg ttgaacaaaa    5460
gcaaatggct gatttcatga ggctatgaat tcgcccttga tctgggtgta tactgcacaa    5520
cctcattgtt cgggaatttg attctcatct cacatacagg cctgtagtat tgcgccctct    5580
ccttctcctt ctccttctcc ttctccaaga gagacttctc tctcatcgcc ctcgtcatca    5640
```

```
atggctgctc gctgtattgt cgttggagca tctcccgata cttctgcaac tgtgataaac    5700
tcatctcagg tgacccatcc gattctgtat cggtgtctcc atctgggct acatctcggg     5760 ccagtctaga tttaaacttt gcagaacctt cactttgggg gatatacact agtgtctctc    5820
ccgtgactac atcaccgaca ccctcaactg taccattatt attgtcattg ttttcctcta    5880
agttctcgct ttggtcntca tccatctctc cttcgggtgc tgtatcactc ttgatgattt    5940
ctctaaccct aatacggaga ctgtgattgc ctgaaataat acccacatct ttcaacttct    6000
gatgaagtga atctccagag atgaccttca tcagcacttg cacatcaacc acatcaccct    6060
ccttttgagc atccctcatg attccataga ctacatcccg tagcgtctcc ttgttcttgt    6120
acttcttaac aacagtctcg ccacagacat ggcccctgat aatcacctcc tgtctctcct    6180
catggccatc ctggtcgcca ttgtcttcgt cgctcggctc aattgccaat gtagcaccct    6240
gtggaagatt gcttagtctg tatggaacag actcatcaac tcntttgcca ttatgcatta    6300
acttgtactt tcgnccttgg ctaagttgaa aatgtttaca tcnwtcntca agtacattgg    6360
acatgattgt ncctgcattg acatttgtcc ggtaagtcct aaacccactc gctagattca    6420
ctgtaggcat attcaatcac gttccgtttg aaaaaaagga aaccaattta ttatctccag    6480
aaatagttgg cgtcttgcat cttgtttggt cttgatcttt cgtgntttttt tttttttctg    6540 tcntttttttt tctcctctct ccaacttttt gattttagt gtaccaaatc gcactgctta    6600
tccacattca tcataaagrg gggggagaa gagggcaga aaataaaagg ccatgtcacg    6660
tgcctgtgca tttatttgtg tgtgtgtcac gtgctcaaaa tgtcttttttt ttacgttttt    6720 aacatttttcc ctttctgtag ttgaatccat ttgcatgagt cgtacatrat gtttgctgta    6780
tttacgttaa gacactaatt caaatgacaa acagctatta ttcttagcca ttaatgcatt    6840
tttgcaaatc tttaactgga tttaactatg gctaggtraa tttgttctgg acatcattgc    6900
cttgacttgt tttagtgccg atgtccttat cacttacact cgtaacacaa cacaacagca    6960
gctaatgttg ttgtgtatcg cttgacccct aataactgat tctttttttga tgaatgttaa    7020 gaagaaacaa acaaraaaat aaaatcaaaa caggcttctt ttgacctctt tcaagagaag    7080
gttttcttgg ttgtttcata taccaagatc tgaatatctt ctattattat acaaaccact    7140
gattatacaa atctattcat cgacagtatg arctacgaaa acacactgat aaaragagtc    7200
atttcttccc cttcttttttc tttttctttt tcttcttctt cttagtatcc ccatcttcat    7260
taactccacc aagtagatcc tctacacccc ccatggccgt taaaaaatgt tcacgaaaga    7320
aatccatatc attattctta ccatccatta aactgtttag atagatggtg atcatctccc    7380
ttgcantgtc tatatcntca acgtcgagta aatgcgacgc aatggtaccc agcttttgtt    7440 cccctttagtg agggttaatt gcgcgcttgg cgtaatcatg gtcatagctg tttcctgtgt    7500
gaaattgtta tccgctcaca attccacaca acatacgagc cggaagcata aagtgtaaag    7560
cctggggtgc ctaatgagtg agctaactca cattaattgc gttgcgctca ctgcccgctt    7620
tccagtcggg aaacctgtcg tgccagctgc attaatgaat cggccaacgc gcgggagag    7680 gcggtttgcg tattgggcgc tcttccgctt cctcgctcac tgactcgctg cgctcggtcg    7740
ttcggctgcg gcgagcggta tcagctcact caaaggcggt aatacggtta ccacagaat    7800 caggggataa cgcaggaaag aacatgtgag caaaaggcca gcaaaaggcc aggaaccgta    7860
aaaaggccgc gttgctggcg ttttccata ggctccgccc ccctgacgag catcacaaaa    7920
atcgacgctc aagtcagagg tggcgaaacc cgacaggact ataaagatac caggcgtttc    7980
```

-continued

```
cccctggaag ctccctcgtg cgctctcctg ttccgaccct gccgcttacc ggatacctgt      8040
ccgcctttct cccttcggga agcgtggcgc tttctcatag ctcacgctgt aggtatctca      8100
gttcggtgta ggtcgttcgc tccaagctgg gctgtgtgca cgaaccccccc gttcagcccg     8160 accgctgcgc cttatccggt aactatcgtc ttgagtccaa cccggtaaga cacgacttat      8220
cgccactggc agcagccact ggtaacagga ttagcagagc gaggtatgta ggcggtgcta      8280
cagagttctt gaagtggtgg cctaactacg gctacactag aaggacagta tttggtatct      8340
gcgctctgct gaagccagtt accttcggaa aaagagttgg tagctcttga tccggcaaac      8400
aaaccaccgc tggtagcggt ggtttttttg tttgcaagca gcagattacg cgcagaaaaa      8460
aaggatctca agaagatcct ttgatctttt ctacggggtc tgacgctcag tggaacgaaa      8520
actcacgtta agggattttg gtcatgagat tatcaaaaag gatcttcacc tagatccttt      8580
taaattaaaa atgaagtttt aaatcaatct aaagtatata tgagtaaact tggtctgaca      8640
gttaccaatg cttaatcagt gaggcaccta tctcagcgat ctgtctattt cgttcatcca      8700
tagttgcctg actccccgtc gtgtagataa ctacgatacg ggagggctta ccatctggcc      8760
ccagtgctgc aatgataccg cgagacccac gctcaccggc tccagattta tcagcaataa      8820
accagccagc cggaagggcc gagcgcagaa gtggtcctgc aactttatcc gcctccatcc      8880
agtctattaa ttgttgccgg gaagctagag taagtagttc gccagttaat agtttgcgca      8940
acgttgttgc cattgctaca ggcatcgtgg tgtcacgctc gtcgtttggt atggcttcat      9000
tcagctccgg ttcccaacga tcaaggcgag ttacatgatc ccccatgttg tgcaaaaaag      9060
cggttagctc cttcggtcct ccgatcgttg tcagaagtaa gttggccgca gtgttatcac      9120
tcatggttat ggcagcactg cataattctc ttactgtcat gccatccgta agatgctttt      9180
ctgtgactgg tgagtactca accaagtcat tctgagaata gtgtatgcgg cgaccgagtt      9240
gctcttgccc ggcgtcaata cgggataata ccgcgccaca tagcagaact ttaaaagtgc      9300
tcatcattgg aaaacgttct tcggggcgaa aactctcaag gatcttaccg ctgttgagat      9360
ccagttcgat gtaacccact cgtgcaccca actgatcttc agcatctttt actttcacca      9420
gcgtttctgg gtgagcaaaa acaggaaggc aaaatgccgc aaaaaaggga ataagggcga      9480
cacggaaatg ttgaatactc atactcttcc ttttcaata ttattgaagc atttatcagg      9540
gttattgtct catgagcgga tacatatttg aatgtattta gaaaaataaa caaatagggg      9600
ttccgcgcac atttccccga aaagtgccac                                       9630
```

<210> SEQ ID NO 13
<211> LENGTH: 6760
<212> TYPE: DNA
<213> ORGANISM: Artificial Sequence
<220> FEATURE:
<223> OTHER INFORMATION: melbiase-invertase-locus A transformation
      sequence
<220> FEATURE:
<221> NAME/KEY: misc_feature
<222> LOCATION: (3991)..(3991)
<223> OTHER INFORMATION: n is a, c, g, or t

<400> SEQUENCE: 13

```
atcgctagcc ttagtgccct cgttaatagt tgaacaaaca ctggcatttg gagtataatg       60
aaaagggatc actaccccccc gcttcctgtt ccgcttctcc cttccggaaa aaccacccac     120
cctttctttt cccccactaa tgtatgaatt tttccgttcc cagggggaatg gcccacttgg     180 ttctctgtta acccacacaa ttttgacgca tcccacacac cttttttttt tctaccccac     240
```

```
actttcccctt gaaaaatctc caatttgaac tggcaatttt caccccccac cacttgcatt    300
cattagtgag tcaatccatc ccgcggtcgg agattcggaa tccacctact ggtaatctgt    360
aatctatatt cccgctgacc ctttataaat gaactattgt cgtcaattgc ggtagtgctc    420
caacaaattg taaggacctt ctttaacctt ttcgattcaa tccatctcca cataaaccta    480
gttgcacaca gctagcatat ggcggccgcg gatccctcga gtttggatga ggcattcaat    540
gtctccatgt ttgaagacca gagaaagtgt aggtaacaca atagccatgg acaattagcg    600
aatccgaata tgtgtactaa cattgtgcct ccaactgaca gctggtcgaa taatgattga    660
aatcatcaaa catatcagag atatatccca gaaccattta caactgttat ttgtatgtat    720
gcattactgt tttacattgt gtcttttccaa atactaacat tgccattatc caatccatac    780
atatatatat atatagatta cacaacgcaa acctcgacag tcgattggtt tacatcgtgt    840
aagcagcctt ttacggaata tgatggacaa ccagatcctc atagatggag acaatgtgca    900
gatagattcc atttatgatg acattgatgt gttttttaaat gcaaataat ctcctatata    960 agtgagttcc gagtctcccc atgcttatct tatcgtgttt tttctgtaaa ttaggtcaaa    1020
gtattcaaac aattccctca atctttccca tttttttgctg agcccccata tcatcaaatt    1080
aacgtatcaa atttcctaat tagtagcccc gtatgttaaa ttagacatgt gtgactgcca    1140
tcccggacag cctacccaat gacacccgcg caccgcacat attgtgttta gtgcgcgccg    1200
tctgctgaag cgactccctg tttgggagga accgagggcg ggttgcccga tcccttgccc    1260
ctcgctcctc ctcctgggct cccccttgca gagggacacc gaggggatcc ctcgtgtgag    1320
agcttggagg tggatggtgg tcaatttct catttgattg aaagatttgt tatattgaaa    1380
attcagtttg tggaagttgt gattaaaagg ttttactgtt tgttctgtag acacattcaa    1440
tatctagata aaatgttaaa gttattgtcc ttgatggtcc cattagcttc tgcagctgtt    1500
atccacagac gtgatgctaa catttcagct attgcatccg aatggaactc cacttctaac    1560
tcttcttcat ctttatcttt aaacagacca gctgtccatt attctccaga ggaaggttgg    1620
atgaacgacc caaacggttt atggtacgat gctaaagagg aagattggca catctactat    1680
caatactatc ctgatgcccc tcattggggt ttgccattga cttggggtca tgcagtctcc    1740
aaagatttga ccgtctggga cgaacaaggt gttgcattcg gtccagagtt tgaaacagca    1800
ggtgcctttt ctggttctat ggttattgat tacaataaca cctccggttt ctttaactca    1860
tccaccgacc caagacaacg tgtcgttgcc atttggactt tggattattc tggctctgaa    1920
acacaacaat tatcttattc tcatgatggt ggttatacat tcaccgaata ttctgacaac    1980
cctgtcttag atattgactc agacgctttt agagatccaa aggttttctg gtatcaaggt    2040
gaagattccg aatcagaagg taactgggtc atgacagttg ccgaagcaga tcgtttctcc    2100
gtcttaatct actcttctcc agaccttaag aattggacct agaatcaaa cttttccaga    2160 gaaggctact taggctataa ctatgagtgt cctggtttag ttaaggtccc atacgtcaaa    2220
aacaccacat acgcatctgc tccaggctca aatatcacct catctggtcc acttcatcca    2280
aattctactg tttctttctc aaattcatcc tctattgcat ggaatgcttc ttccgttcca    2340
cttaacatta ctttatccaa ttctaccttg gttgatgaaa cttctcaatt ggaagaagtt    2400
ggttacgcat gggttatgat tgtctcattc aatcctggct ccatttttagg cggttccggt    2460 actgaatact tcatcggtga ctttaatggt acacacttcg agccacttga taagcaaact    2520
agattcttag atttgggtaa agattactac gctttgcaaa ctttcttcaa taccccaaac    2580
gaggttgacg ttttgggtat cgcatgggcc tctaattggc aatatgctaa ccaagttcca    2640
```

```
acagatccat ggagatcatc catgtccttg gttagaaact tcactatcac tgaatacaac    2700
atcaattcta atactactgc attggtcttg aactctcaac cagttttaga ttttacctct    2760
ttaagaaaga acggcacatc atatacttta gagaatctta cattaaactc ctcttctcac    2820
gaggttttgg aatttgaaga tcctaccggt gttttcgaat tttcccttga atattccgtc    2880
aactttaccg gtattcacaa ctgggttttt accgacttgt ccttgtattt ccaaggtgat    2940
aaggattcag atgaatactt gagacttggt tacgaagcta actccaagca gttctttta    3000 gatagaggtc attctaacat tccatttgtt caagaaaatc cattcttcac tcagagactt    3060
tcagtttcca atcctccatc ctccaactcc tccaccttcg atgtctacgg tattgttgac    3120
agaaatatca ttgaattgta tttcaacaat ggtactgtta cctctactaa caccttttc    3180 ttctccactg gtaacaatat tggttccatc attgttaagt ctggtgttga tgacgtctat    3240
gaaattgaat cattgaaggt taatcagttt tacgttgact aattaattaa catctgaatg    3300
taaaatgaac attaaaatga attactaaac tttacgtcta ctttacaatc tataaacttt    3360
gtttaatcat ataacgaaat acactaatac acaatcctgt acgtatgtaa tactttatc    3420 catcaaggat tgagaaaaaa aagtaatgat tccctgggcc attaaaactt agaccccaa    3480 gcttggatag gtcactctct attttcgttt ctcccttccc tgatagaagg gtgatatgta    3540
attaagaata atatataatt ttataataaa agaattcgcc cttacctgca gggataactt    3600
cgtataatgt atgctatacg aagttatgct gcaacggcaa catcaatgtc cacgtttaca    3660
cacctacatt tatatctata tttatattta tatttattta tttatgctac ttagcttcta    3720
tagttagtta atgcactcac gatattcaaa attgacaccc ttcaactact ccctactatt    3780
gtctactact gtctactact cctctttact atagctgctc caataggct ccaccaatag    3840 gctctgtcaa tacattttgc gccgccacct ttcaggttgt gtcactcctg aaggaccata    3900
ttgggtaatc gtgcaatttc tggaagagag tgccgcgaga agtgaggccc ccactgtaaa    3960
tcctcgaggg ggcatggagt atggggcatg naggatggag gatgggggg ggggggaaa     4020 ataggtagcg aaaggacccg ctatcacccc acccggagaa ctcgttgccg ggaagtcata    4080
tttcgacact ccggggagtc tataaaaggc gggttttgtc ttttgccagt tgatgttgct    4140
gagaggactt gtttgccgtt tcttccgatt taacagtata gaatcaacca ctgttaatta    4200
tacacgttat actaacacaa caaaaacaaa acaacgaca acaacaacaa caatgtttgc     4260
tttctacttt ctcaccgcat gcaccacttt gaagggtgtt ttcggagttt ctccgagtta    4320
caatggtctt ggtctcaccc cacagatggg ttgggacagc tggaatacgt ttgcctgcga    4380
tgtcagtgaa cagctacttc tagacactgc tgatagaatt tctgacttgg ggctaaagga    4440
tatgggttac aagtatgtca tcctagatga ctgttggtct agcggcaggg attccgacgg    4500
tttcctcgtt gcagacaagc acaaatttcc caacggtatg ggccatgttg cagaccacct    4560
gcataataac agctttcttt tcggtatgta ttcgtctgct ggtgagtaca cctgtgctgg    4620
gtaccctggg tctctggggc gtgaggaaga agatgctcaa ttctttgcaa ataaccgcgt    4680
tgactacttg aagtatgata attgttacaa taaaggtcaa tttggtacac cagacgtttc    4740
ttaccaccgt tacaaggcca tgtcagatgc tttgaataaa actggtaggc ctattttcta    4800
ttctctatgt aactggggtc aggatttgac attttactgg ggctctggta tcgccaattc    4860
ttggagaatg agcggagata ttactgctga gttcacccgt ccagatagca gatgtccctg    4920
tgacggtgac gaatatgatt gcaagtacgc cggtttccat tgttctatta tgaatattct    4980
```

| | |
|---|---|
| taacaaggca gctccaatgg ggcaaaatgc aggtgttggt ggttggaacg atctggacaa | 5040 |
| tctagaggtc ggagtcggta atttgactga cgatgaggaa aaggcccatt tctctatgtg | 5100 |
| ggcaatggta aagtccccac ttatcattgg tgccgacgtg aatcacttaa aggcatcttc | 5160 |
| gtactcgatc tacagtcaag cctctgtcat cgcaattaat caagatccaa agggtattcc | 5220 |
| agccacaaga gtctggagat attatgtttc agacaccgat gaatatggac aaggtgaaat | 5280 |
| tcaaatgtgg agtggtccgc ttgacaatgg tgaccaagtg gttgctttat tgaatggagg | 5340 |
| aagcgtagca agaccaatga acacgacctt ggaagagatt ttctttgaca gcaatttggg | 5400 |
| ttcaaaggaa ctgacatcga cttgggatat ttacgactta tgggccaaca gagttgacaa | 5460 |
| ctctacggcg tctgctatcc ttgaacagaa taaggcagcc accggtattc tctacaatgc | 5520 |
| tacagagcag tcttataaag acggtttgtc taagaatgat acaagactgt ttggccagaa | 5580 |
| aattggtagt ctttctccaa atgctatact taacacaact gttccagctc atggtatcgc | 5640 |
| cttctatagg ttgagaccct cggcttaagc tcaatgttga gcaaagcagg acgagaaaaa | 5700 |
| aaaaaataat gattgttaag aagttcatga aaaaaaaaag gaaaaatact caaatactta | 5760 |
| taacagagtg attaaataat aaacggcagt atacctatc aggtattgag atagttttat | 5820 |
| ttttgtaggt atataatctg aagcctttga actattttct cgtatatatc atggagtata | 5880 |
| cattgcatta gcaacattgc atactagttc ataacttcgt ataatgtatg ctatacgaag | 5940 |
| ttattaatta caagggcga attccttgat ttatatacac ctttgcgagc tctaatgatt | 6000 |
| caagaaaaag ttcaaataaa ctaatggatc aacctatttc gaccctttct tcattgctac | 6060 |
| ttcttcctta agcaacagat gattaagtag atactgtttt tttagccaat agtatctcgc | 6120 |
| cgaggagtta tacttgacta gctcttgctc aagaatcttc ctaagacgta ctagcctagc | 6180 |
| atagtaatct gtttgtttct gtattgtttg ttctaactgt tctacagtca ttgaatcaat | 6240 |
| atctccaatg tcttcgacgt tgacaacttt cccccccttg gcagcattct cttttttgtt | 6300 |
| ggaatacgac attaaagatt ccttgatttt ctgggtacct tcaatgacca ttgagggatt | 6360 |
| aaatttgatt tctttgattt tataatggtc ggctattagc tcttccactt cgtcatcatg | 6420 |
| atcatcagat atgtcacgtt gccttttcaa tttattaaaa ttgtttatca gtttattgtg | 6480 |
| atcttgtatc aattcattgc gtactctttt ctcaatatca aaagctattt tcttcccgct | 6540 |
| agactcaaaa tcaactctga agtcattttc tcgctggaat tcatgtattt catgattaa | 6600 |
| ttctctattg atattctcgt atgcatcctg taaactgttg ccgttgatat tatgaaccgc | 6660 |
| ctttaaatgt ttcaataagg catctgctct agtaaatgcc ttcagacatt caggtaataa | 6720 |
| acagtaaaat ggcttctcgg ctgtatgcgt cctaatgttt | 6760 |

<210> SEQ ID NO 14
<211> LENGTH: 575
<212> TYPE: PRT
<213> ORGANISM: Issatchenkia orientalis

<400> SEQUENCE: 14

Met Thr Asp Lys Ile Ser Leu Gly Thr Tyr Leu Phe Glu Lys Leu Lys
1               5                   10                  15

Glu Ala Gly Ser Tyr Ser Ile Phe Gly Val Pro Gly Asp Phe Asn Leu
            20                  25                  30

Ala Leu Leu Asp His Val Lys Glu Val Glu Gly Ile Arg Trp Val Gly
        35                  40                  45

Asn Ala Asn Glu Leu Asn Ala Gly Tyr Glu Ala Asp Gly Tyr Ala Arg
    50                  55                  60

```
Ile Asn Gly Phe Ala Ser Leu Ile Thr Thr Phe Val Gly Glu Leu
 65                  70                  75                  80

Ser Ala Val Asn Ala Ile Ala Gly Ser Tyr Ala Glu His Val Pro Leu
             85                  90                  95

Ile His Ile Val Gly Met Pro Ser Leu Ser Ala Met Lys Asn Asn Leu
            100                 105                 110

Leu Leu His His Thr Leu Gly Asp Thr Arg Phe Asp Asn Phe Thr Glu
        115                 120                 125

Met Ser Lys Lys Ile Ser Ala Lys Val Glu Ile Val Tyr Asp Leu Glu
        130                 135                 140

Ser Ala Pro Lys Leu Ile Asn Asn Leu Ile Glu Thr Ala Tyr His Thr
145                 150                 155                 160

Lys Arg Pro Val Tyr Leu Gly Leu Pro Ser Asn Phe Ala Asp Glu Leu
                165                 170                 175

Val Pro Ala Ala Leu Val Lys Glu Asn Lys Leu His Leu Glu Glu Pro
            180                 185                 190

Leu Asn Asn Pro Val Ala Glu Glu Phe Ile His Asn Val Val Glu
        195                 200                 205

Met Val Lys Lys Ala Glu Lys Pro Ile Ile Leu Val Asp Ala Cys Ala
    210                 215                 220

Ala Arg His Asn Ile Ser Lys Glu Val Arg Glu Leu Ala Lys Leu Thr
225                 230                 235                 240

Lys Phe Pro Val Phe Thr Thr Pro Met Gly Lys Ser Thr Val Asp Glu
                245                 250                 255

Asp Asp Glu Glu Phe Phe Gly Leu Tyr Leu Gly Ser Leu Ser Ala Pro
            260                 265                 270

Asp Val Lys Asp Ile Val Gly Pro Thr Asp Cys Ile Leu Ser Leu Gly
        275                 280                 285

Gly Leu Pro Ser Asp Phe Asn Thr Gly Ser Phe Ser Tyr Gly Tyr Thr
    290                 295                 300

Thr Lys Asn Val Val Glu Phe His Ser Asn Tyr Cys Lys Phe Lys Ser
305                 310                 315                 320

Ala Thr Tyr Glu Asn Leu Met Met Lys Gly Ala Val Gln Arg Leu Ile
                325                 330                 335

Ser Glu Leu Lys Asn Ile Lys Tyr Ser Asn Val Ser Thr Leu Ser Pro
            340                 345                 350

Pro Lys Ser Lys Phe Ala Tyr Glu Ser Ala Lys Val Ala Pro Glu Gly
        355                 360                 365

Ile Ile Thr Gln Asp Tyr Leu Trp Lys Arg Leu Ser Tyr Phe Leu Lys
    370                 375                 380

Pro Arg Asp Ile Ile Val Thr Glu Thr Gly Thr Ser Ser Phe Gly Val
385                 390                 395                 400

Leu Ala Thr His Leu Pro Arg Asp Ser Lys Ser Ile Ser Gln Val Leu
                405                 410                 415

Trp Gly Ser Ile Gly Phe Ser Leu Pro Ala Ala Val Gly Ala Ala Phe
            420                 425                 430

Ala Ala Glu Asp Ala His Lys Gln Thr Gly Glu Gln Glu Arg Arg Thr
        435                 440                 445

Val Leu Phe Ile Gly Asp Gly Ser Leu Gln Leu Thr Val Gln Ser Ile
    450                 455                 460

Ser Asp Ala Ala Arg Trp Asn Ile Lys Pro Tyr Ile Phe Ile Leu Asn
465                 470                 475                 480
```

```
Asn Arg Gly Tyr Thr Ile Glu Lys Leu Ile His Gly Arg His Glu Asp
                485                 490                 495

Tyr Asn Gln Ile Gln Pro Trp Asp His Gln Leu Leu Lys Leu Phe
            500                 505                 510

Ala Asp Lys Thr Gln Tyr Glu Asn His Val Val Lys Ser Ala Lys Asp
            515                 520                 525

Leu Asp Ala Leu Met Lys Asp Glu Ala Phe Asn Lys Glu Asp Lys Ile
530                 535                 540

Arg Val Ile Glu Leu Phe Leu Asp Glu Phe Asp Ala Pro Glu Ile Leu
545                 550                 555                 560

Val Ala Gln Ala Lys Leu Ser Asp Glu Ile Asn Ser Lys Ala Ala
            565                 570                 575

<210> SEQ ID NO 15
<211> LENGTH: 532
<212> TYPE: PRT
<213> ORGANISM: Saccharomyces cerevisiae

<400> SEQUENCE: 15

Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
            20                  25                  30

Phe Thr Pro Asn Lys Gly Trp Met Asn Asp Pro Asn Gly Leu Trp Tyr
        35                  40                  45

Asp Glu Lys Asp Ala Lys Trp His Leu Tyr Phe Gln Tyr Asn Pro Asn
    50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285
```

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320

Pro Trp Arg Ser Ser Met Ser Leu Val Arg Lys Phe Ser Leu Asn Thr
                325                 330                 335

Glu Tyr Gln Ala Asn Pro Glu Thr Glu Leu Ile Asn Leu Lys Ala Glu
            340                 345                 350

Pro Ile Leu Asn Ile Ser Asn Ala Gly Pro Trp Ser Arg Phe Ala Thr
        355                 360                 365

Asn Thr Thr Leu Thr Lys Ala Asn Ser Tyr Asn Val Asp Leu Ser Asn
    370                 375                 380

Ser Thr Gly Thr Leu Glu Phe Glu Leu Val Tyr Ala Val Asn Thr Thr
385                 390                 395                 400

Gln Thr Ile Ser Lys Ser Val Phe Ala Asp Leu Ser Leu Trp Phe Lys
                405                 410                 415

Gly Leu Glu Asp Pro Glu Glu Tyr Leu Arg Met Gly Phe Glu Val Ser
            420                 425                 430

Ala Ser Ser Phe Phe Leu Asp Arg Gly Asn Ser Lys Val Lys Phe Val
        435                 440                 445

Lys Glu Asn Pro Tyr Phe Thr Asn Arg Met Ser Val Asn Asn Gln Pro
    450                 455                 460

Phe Lys Ser Glu Asn Asp Leu Ser Tyr Tyr Lys Val Tyr Gly Leu Leu
465                 470                 475                 480

Asp Gln Asn Ile Leu Glu Leu Tyr Phe Asn Asp Gly Asp Val Val Ser
                485                 490                 495

Thr Asn Thr Tyr Phe Met Thr Gly Asn Ala Leu Gly Ser Val Asn
            500                 505                 510

Met Thr Thr Gly Val Asp Asn Leu Phe Tyr Ile Asp Lys Phe Gln Val
        515                 520                 525

Arg Glu Val Lys
    530

<210> SEQ ID NO 16
<211> LENGTH: 581
<212> TYPE: PRT
<213> ORGANISM: Schizosaccharomyces pombe

<400> SEQUENCE: 16

Met Phe Leu Lys Tyr Ile Leu Ala Ser Gly Ile Cys Leu Val Ser Leu
1               5                   10                  15

Leu Ser Ser Thr Asn Ala Ala Pro Arg His Leu Tyr Val Lys Arg Tyr
            20                  25                  30

Pro Val Ile Tyr Asn Ala Ser Asn Ile Thr Glu Val Ser Asn Ser Thr
        35                  40                  45

Thr Val Pro Pro Pro Phe Val Asn Thr Thr Ala Pro Asn Gly Thr
    50                  55                  60

Cys Leu Gly Asn Tyr Asn Glu Tyr Leu Pro Ser Gly Tyr Tyr Asn Ala
65                  70                  75                  80

Thr Asp Arg Pro Lys Ile His Phe Thr Pro Ser Ser Gly Phe Met Asn
                85                  90                  95

Asp Pro Asn Gly Leu Val Tyr Thr Gly Gly Val Tyr His Met Phe Phe
            100                 105                 110

Gln Tyr Ser Pro Lys Thr Leu Thr Ala Gly Glu Val His Trp Gly His

```
            115                 120                 125
Thr Val Ser Lys Asp Leu Ile His Trp Glu Asn Tyr Pro Ile Ala Ile
130                 135                 140

Tyr Pro Asp Glu His Glu Asn Gly Val Leu Ser Leu Pro Phe Ser Gly
145                 150                 155                 160

Ser Ala Val Val Asp Val His Asn Ser Ser Gly Leu Phe Ser Asn Asp
                    165                 170                 175

Thr Ile Pro Glu Glu Arg Ile Val Leu Ile Tyr Thr Asp His Trp Thr
                    180                 185                 190

Gly Val Ala Glu Arg Gln Ala Ile Ala Tyr Thr Thr Asp Gly Gly Tyr
                    195                 200                 205

Thr Phe Lys Lys Tyr Ser Gly Asn Pro Val Leu Asp Ile Asn Ser Leu
                    210                 215                 220

Gln Phe Arg Asp Pro Lys Val Ile Trp Asp Phe Asp Ala Asn Arg Trp
225                 230                 235                 240

Val Met Ile Val Ala Met Ser Gln Asn Tyr Gly Ile Ala Phe Tyr Ser
                    245                 250                 255

Ser Tyr Asp Leu Ile His Trp Thr Glu Leu Ser Val Phe Ser Thr Ser
                    260                 265                 270

Gly Tyr Leu Gly Leu Gln Tyr Glu Cys Pro Gly Met Ala Arg Val Pro
                    275                 280                 285

Val Glu Gly Thr Asp Glu Tyr Lys Trp Val Leu Phe Ile Ser Ile Asn
290                 295                 300

Pro Gly Ala Pro Leu Gly Gly Ser Val Val Gln Tyr Phe Val Gly Asp
305                 310                 315                 320

Trp Asn Gly Thr Asn Phe Val Pro Asp Asp Gly Gln Thr Arg Phe Val
                    325                 330                 335

Asp Leu Gly Lys Asp Phe Tyr Ala Ser Ala Leu Tyr His Ser Ser Ser
                    340                 345                 350

Ala Asn Ala Asp Val Ile Gly Val Gly Trp Ala Ser Asn Trp Gln Tyr
                    355                 360                 365

Thr Asn Gln Ala Pro Thr Gln Val Phe Arg Ser Ala Met Thr Val Ala
                    370                 375                 380

Arg Lys Phe Thr Leu Arg Asp Val Pro Gln Asn Pro Met Thr Asn Leu
385                 390                 395                 400

Thr Ser Leu Ile Gln Thr Pro Leu Asn Val Ser Leu Leu Arg Asp Glu
                    405                 410                 415

Thr Leu Phe Thr Ala Pro Val Ile Asn Ser Ser Ser Leu Ser Gly
                    420                 425                 430

Ser Pro Ile Thr Leu Pro Ser Asn Thr Ala Phe Glu Phe Asn Val Thr
                    435                 440                 445

Leu Ser Ile Asn Tyr Thr Glu Gly Cys Thr Thr Gly Tyr Cys Leu Gly
                    450                 455                 460

Arg Ile Ile Ile Asp Ser Asp Pro Tyr Arg Leu Gln Ser Ile Ser
465                 470                 475                 480

Val Asp Val Asp Phe Ala Ala Ser Thr Leu Val Ile Asn Arg Ala Lys
                    485                 490                 495

Ala Gln Met Gly Trp Phe Asn Ser Leu Phe Thr Pro Ser Phe Ala Asn
                    500                 505                 510

Asp Ile Tyr Ile Tyr Gly Asn Val Thr Leu Tyr Gly Ile Val Asp Asn
                    515                 520                 525

Gly Leu Leu Glu Leu Tyr Val Asn Asn Gly Glu Lys Tyr Thr Asn
530                 535                 540
```

Asp Phe Phe Phe Leu Gln Gly Ala Thr Pro Gly Gln Ile Ser Phe Ala
545                 550                 555                 560

Ala Phe Gln Gly Val Ser Phe Asn Asn Val Thr Val Thr Pro Leu Lys
            565                 570                 575

Thr Ile Trp Asn Cys
            580

<210> SEQ ID NO 17
<211> LENGTH: 627
<212> TYPE: PRT
<213> ORGANISM: Aspergillus niger

<400> SEQUENCE: 17

Met His Ile Leu Pro Gly Ser Gln His Ala Glu Leu Asp Asn Ser
1               5                   10                  15

Gly Thr Leu Ile His Ser Val His Cys Asp Pro Glu Gln Lys Ala Lys
            20                  25                  30

Asn Ile Pro Gln Ser Thr Gly Ile Ala Gln Ala Ser Ser Glu Trp Arg
            35                  40                  45

Pro Ser Tyr His Leu Ala Ala Pro Arg Gly Trp Met Asn Asp Pro Cys
50                  55                  60

Gly Leu Gly Tyr Asp Pro Thr Thr Gly Leu Tyr His Leu Ser Phe Gln
65                  70                  75                  80

Trp Asn Pro His Gly Asn Asp Trp Gly Asn Ile Ser Trp Gly His Ala
                85                  90                  95

Thr Ser Ser Asp Leu Val Ser Trp Gln Ile Ser Pro Glu Pro Cys Leu
            100                 105                 110

Thr Pro Ser Ala Glu Tyr Asp Arg Cys Gly Val Phe Thr Gly Cys Phe
        115                 120                 125

Arg Ser His Gly Pro Asp Gly Lys Pro Gly Val Leu Thr Tyr Val Tyr
130                 135                 140

Thr Ser Val Asn His Leu Pro Leu His Tyr Thr Leu Pro Tyr Val Lys
145                 150                 155                 160

Gly Ser Glu Ser Leu Ser Ile Ala Val Ser Arg Asp His Gly Lys Thr
                165                 170                 175

Trp Gln Arg Ile Asp Ser Asn Pro Ile His Pro Gly Ala Pro Ala Gly
            180                 185                 190

Leu Glu Val Thr Gly Trp Arg Asp Pro Tyr Leu Asn Cys Trp Pro Ser
        195                 200                 205

Leu Arg Ala Gln Arg Gln Gly Val Ala Ser Pro Asp Leu Tyr Gly
210                 215                 220

Phe Ile Ser Gly Gly Ile Ala Lys Glu Ser Pro Thr Val Phe Val Tyr
225                 230                 235                 240

Val Val Asn Pro Asp Asn Leu Thr Glu Trp Thr Tyr Ile Gly Pro Leu
            245                 250                 255

Leu His Val Gly Leu Asn Tyr Arg Pro Ser Arg Trp Ser Gly Asp Leu
        260                 265                 270

Gly Val Asn Trp Glu Val Ala Asn Phe Phe Thr Leu Thr Asp Gly Gly
    275                 280                 285

Val Ser Arg Asp Ile Val Ile Phe Gly Ala Glu Gly Cys Leu Ser Cys
            290                 295                 300

Glu Val Gly Ser Lys Arg Val Pro Arg Ser Leu Leu Trp Met Cys Ile
305                 310                 315                 320

Asn Val Arg Pro Gly Leu Gln Ala Gln Ser Ser Gly Glu Pro Leu Ala

```
                        325                 330                 335
Asp Tyr Ser Phe Ser Gly Ile Phe Asp His Gly Cys Cys Tyr Ala Ala
                340                 345                 350

Asn Ser Phe Trp Asp Pro Val Thr Glu Glu Tyr Val Val Tyr Cys Trp
                355                 360                 365

Ile Thr Glu Glu Asp Leu Pro Asp Arg Leu Arg His Arg Gln Gly Trp
                370                 375                 380

Ser Gly Ile Met Ser Leu Pro Arg Leu Val Arg Leu Val Thr Leu His
385                 390                 395                 400

Asn Val Lys Arg Ala His Gln Ser Lys Leu Glu Ser Ile Thr Ser Val
                405                 410                 415

Glu Ile Glu Arg His Ser Gln Gly Thr Gln Val Arg Thr Leu Ser Val
                420                 425                 430

Arg Pro Asp Pro Arg Leu Asn Ile Leu Arg Thr Ser Ala Arg Glu Leu
                435                 440                 445

His Leu Ser Asn Val Gln Leu Gly Ser Val Ala His Gln Pro Pro Ala
                450                 455                 460

Phe Leu Pro Leu Arg Thr Ala Arg Trp Glu Met Thr Ala Thr Phe Val
465                 470                 475                 480

Ile Gly Thr His Cys Ala Ala Val Gly Leu Glu Ile Gly His Ser Pro
                485                 490                 495

Asp Phe His Gln Arg Thr Thr Leu Ser Trp Ile Pro Tyr Asp Glu Thr
                500                 505                 510

Phe Thr Ile Glu Arg Pro Pro Leu His Asp Ala Gly Ile Asn His Val
                515                 520                 525

Pro Glu Thr Ala Pro His Thr Leu Phe Thr Phe Cys Asn Asn Glu Gly
        530                 535                 540

Glu Glu Val Thr Glu Pro Leu Gln Ile His Ala Tyr Phe Asp Ala Ser
545                 550                 555                 560

Val Leu Glu Val Phe Val Asn Ser Arg Thr Val Ile Ser Thr Arg Ile
                565                 570                 575

Tyr Thr Pro His Ala Gln Val Cys Thr Gly Leu Lys Phe Phe Ala Ser
                580                 585                 590

Ala Thr Glu Ser Gln Pro Lys Pro Ser Thr Ser Ala Pro Ala Ala Val
        595                 600                 605

Leu Val Arg Ala Asp Ile Trp Asp Gly Leu Ser Val Ile Arg Asp Glu
        610                 615                 620

Ile Lys His
625
```